United States Patent
Rapalo et al.

(10) Patent No.: US 11,974,787 B2
(45) Date of Patent: May 7, 2024

(54) BONE PLATE

(71) Applicant: Smith & Nephew, Inc., Memphis, TN (US)

(72) Inventors: Gabriel E. Rapalo, Memphis, TN (US); Timothy J. Petteys, Bartlett, TN (US); Nicholas S. Ritchey, Collierville, TN (US); Charles R. Bennett, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 17/993,315

(22) Filed: Nov. 23, 2022

(65) Prior Publication Data

US 2023/0089488 A1  Mar. 23, 2023

Related U.S. Application Data

(63) Continuation of application No. 17/222,503, filed on Apr. 5, 2021, now Pat. No. 11,534,213, which is a
(Continued)

(51) Int. Cl.
*A61B 17/80* (2006.01)
*A61B 17/68* (2006.01)

(52) U.S. Cl.
CPC ...... *A61B 17/8014* (2013.01); *A61B 17/8052* (2013.01); *A61B 17/8057* (2013.01); *A61B 2017/681* (2013.01)

(58) Field of Classification Search
CPC ............ A61B 17/8014; A61B 17/8052; A61B 17/8057; A61B 17/8004; A61B 2017/681
See application file for complete search history.

(56) References Cited

U.S. PATENT DOCUMENTS

| 300,146 A | 6/1884 | Sinnett |
| 351,751 A | 11/1886 | Douglas |

(Continued)

FOREIGN PATENT DOCUMENTS

| AU | 754857 B2 | 11/2002 |
| CA | 2047521 A1 | 1/1992 |

(Continued)

OTHER PUBLICATIONS

International Search Report and Written Opinion for International Application No. PCT/US2016/051864, dated Feb. 24, 2017.
(Continued)

*Primary Examiner* — Tracy L Kamikawa
(74) *Attorney, Agent, or Firm* — KDW Firm PLLC

(57) ABSTRACT

Variable angle holes in bone plates structured to facilitate the formation of axial compression or tension of a bone, or which can assist in bone distraction. The variable angle hole can extend about a central axis and includes an inwardly extending wedge wall. The variable angle hole can be sized to receive insertion of a fixation element at a location at which a central longitudinal axis of the fixation element is axially offset from the central axis of the variable angle hole by an offset distance at least when the fixation element is initially driven into bone at least in a transverse direction. The wedge wall can be configured to be engaged by a portion of the fixation element in a manner that axially displaces at least one of the bone plate, the fixation element, and/or bone(s) in a direction that can generally reduce or increase the offset distance.

13 Claims, 15 Drawing Sheets

Related U.S. Application Data continuation of application No. 15/758,207, filed as application No. PCT/US2016/051864 on Sep. 15, 2016, now Pat. No. 10,993,750.

(60) Provisional application No. 62/220,562, filed on Sep. 18, 2015.

(56) References Cited

U.S. PATENT DOCUMENTS

| | | |
|---|---|---|
| 382,670 A | 5/1888 | Trovillion |
| 544,606 A | 8/1895 | Balsley |
| 545,331 A | 8/1895 | Balsley |
| 565,808 A | 8/1896 | Staples |
| 575,631 A | 1/1897 | Brooks |
| 583,158 A | 5/1897 | Upham |
| 637,990 A | 11/1899 | Hoepner |
| 651,949 A | 6/1900 | Lillie |
| 689,722 A | 12/1901 | Hoover |
| 766,270 A | 8/1904 | Lapham |
| 775,427 A | 11/1904 | Lusted, Sr. |
| 902,040 A | 10/1908 | Wyckoff |
| 1,025,008 A | 4/1912 | Miner |
| 1,105,105 A | 7/1914 | Sherman |
| 1,275,810 A | 8/1918 | White |
| 1,575,149 A | 3/1926 | Craig et al. |
| 1,755,588 A | 4/1930 | Bronk |
| 1,925,385 A | 9/1933 | Humes et al. |
| 2,010,913 A | 8/1935 | Bruce et al. |
| 2,133,859 A | 10/1938 | Hawley |
| 2,152,977 A | 4/1939 | John |
| 2,501,978 A | 3/1950 | Heins |
| 2,524,167 A | 10/1950 | Frank |
| 2,560,912 A | 7/1951 | George |
| 2,667,194 A | 1/1954 | Fischer et al. |
| 2,756,791 A | 7/1956 | Benjamin |
| 3,056,441 A | 10/1962 | Helms |
| 3,279,510 A | 10/1966 | Dreyer et al. |
| 3,347,293 A | 10/1967 | Clark |
| 3,409,058 A | 11/1968 | La |
| 3,547,114 A | 12/1970 | Haboush |
| 3,552,389 A | 1/1971 | Allgower et al. |
| 3,630,261 A | 12/1971 | Gley |
| 3,662,797 A | 5/1972 | Healis |
| 3,668,972 A | 6/1972 | Allgower et al. |
| 3,716,050 A | 2/1973 | Johnston |
| 3,739,825 A | 6/1973 | Knox |
| 3,741,205 A | 6/1973 | Markolf et al. |
| 3,744,488 A | 7/1973 | Cox |
| 3,779,240 A | 12/1973 | Kondo |
| 3,782,432 A | 1/1974 | Allen |
| 3,866,607 A | 2/1975 | Forsythe et al. |
| 3,906,550 A | 9/1975 | Rostoker et al. |
| 3,935,762 A | 2/1976 | Tudisco |
| RE28,841 E | 6/1976 | Allgower et al. |
| 4,059,102 A | 11/1977 | Devas |
| 4,060,114 A | 11/1977 | Matsushima |
| 4,096,896 A | 6/1978 | Engel |
| 4,219,015 A | 8/1980 | Steinemann |
| 4,246,811 A | 1/1981 | Bondhus et al. |
| 4,263,904 A | 4/1981 | Judet |
| 4,338,926 A | 7/1982 | Kummer et al. |
| 4,364,382 A | 12/1982 | Mennen |
| 4,388,921 A | 6/1983 | Sutter et al. |
| 4,408,601 A | 10/1983 | Wenk |
| RE31,628 E | 7/1984 | Allgower et al. |
| 4,484,570 A | 11/1984 | Sutter et al. |
| 4,493,317 A | 1/1985 | Klaue |
| 4,513,744 A | 4/1985 | Klaue |
| 4,535,658 A | 8/1985 | Molinari |
| 4,564,007 A | 1/1986 | Coombs et al. |
| 4,565,193 A | 1/1986 | Streli |
| 4,573,458 A | 3/1986 | Lower |
| 4,683,878 A | 8/1987 | Carter |
| 4,704,929 A | 11/1987 | Osada |
| 4,791,918 A | 12/1988 | Von |
| 4,797,948 A | 1/1989 | Milliorn et al. |
| 4,838,252 A | 6/1989 | Klaue |
| 4,927,421 A | 5/1990 | Goble et al. |
| 4,978,349 A | 12/1990 | Frigg |
| 4,988,350 A | 1/1991 | Herzberg |
| 5,002,544 A | 3/1991 | Klaue et al. |
| 5,006,120 A | 4/1991 | Carter |
| 5,041,114 A | 8/1991 | Chapman et al. |
| 5,053,036 A | 10/1991 | Perren et al. |
| 5,085,660 A | 2/1992 | Lin |
| 5,129,901 A | 7/1992 | Decoste |
| 5,151,103 A | 9/1992 | Tepic et al. |
| 5,190,544 A | 3/1993 | Chapman et al. |
| 5,192,281 A | 3/1993 | de la Caffiniere |
| 5,197,966 A | 3/1993 | Sommerkamp |
| 5,198,308 A | 3/1993 | Shelly et al. |
| 5,237,893 A | 8/1993 | Ryder et al. |
| 5,259,398 A | 11/1993 | Vrespa |
| 5,269,784 A | 12/1993 | Mast |
| 5,275,601 A | 1/1994 | Gogolewski et al. |
| 5,304,180 A | 4/1994 | Slocum |
| 5,312,410 A | 5/1994 | Miller et al. |
| 5,324,290 A | 6/1994 | Zdeblick et al. |
| 5,324,291 A | 6/1994 | Ries et al. |
| 5,356,410 A | 10/1994 | Pennig |
| 5,360,452 A | 11/1994 | Engelhardt et al. |
| 5,364,398 A | 11/1994 | Chapman et al. |
| 5,364,399 A | 11/1994 | Lowery et al. |
| 5,395,374 A | 3/1995 | Miller et al. |
| 5,415,658 A | 5/1995 | Kilpela et al. |
| 5,423,820 A | 6/1995 | Miller et al. |
| 5,423,826 A | 6/1995 | Coates et al. |
| 5,429,641 A | 7/1995 | Golfried |
| 5,431,659 A | 7/1995 | Ross et al. |
| 5,470,333 A | 11/1995 | Ray |
| 5,474,553 A | 12/1995 | Baumgart |
| 5,487,743 A | 1/1996 | Laurain et al. |
| 5,514,138 A | 5/1996 | McCarthy |
| 5,520,690 A | 5/1996 | Errico et al. |
| 5,522,902 A | 6/1996 | Yuan et al. |
| 5,527,310 A | 6/1996 | Cole et al. |
| 5,531,143 A | 7/1996 | Habermehl et al. |
| 5,531,746 A | 7/1996 | Errico et al. |
| 5,531,748 A | 7/1996 | de la Caffiniere |
| 5,534,932 A | 7/1996 | Van et al. |
| 5,536,127 A | 7/1996 | Pennig |
| 5,569,253 A | 10/1996 | Farris et al. |
| 5,578,034 A | 11/1996 | Estes |
| 5,591,168 A | 1/1997 | Judet et al. |
| 5,601,553 A | 2/1997 | Trebing et al. |
| 5,607,426 A | 3/1997 | Ralph et al. |
| 5,607,428 A | 3/1997 | Lin |
| 5,643,265 A | 7/1997 | Errico et al. |
| 5,647,873 A | 7/1997 | Errico et al. |
| 5,665,088 A | 9/1997 | Gil et al. |
| 5,665,089 A | 9/1997 | Dall et al. |
| 5,676,667 A | 10/1997 | Hausman |
| 5,702,399 A | 12/1997 | Kilpela et al. |
| 5,709,686 A | 1/1998 | Talos et al. |
| 5,713,900 A | 2/1998 | Benzel et al. |
| 5,725,588 A | 3/1998 | Errico et al. |
| 5,733,287 A | 3/1998 | Tepic et al. |
| 5,735,853 A | 4/1998 | Olerud |
| 5,741,258 A | 4/1998 | Klaue et al. |
| 5,749,872 A | 5/1998 | Kyle et al. |
| 5,769,850 A | 6/1998 | Chin |
| 5,772,662 A | 6/1998 | Chapman et al. |
| 5,776,196 A | 7/1998 | Matsuzaki et al. |
| 5,788,697 A | 8/1998 | Kilpela et al. |
| 5,797,912 A | 8/1998 | Runciman et al. |
| 5,810,823 A | 9/1998 | Klaue et al. |
| 5,824,247 A | 10/1998 | Tunc |
| 5,876,402 A | 3/1999 | Errico et al. |
| 5,888,204 A | 3/1999 | Ralph et al. |
| 5,893,856 A | 4/1999 | Jacob et al. |
| 5,902,305 A | 5/1999 | Beger et al. |
| 5,904,683 A | 5/1999 | Pohndorf et al. |
| 5,904,684 A | 5/1999 | Rooks |

(56) References Cited

U.S. PATENT DOCUMENTS

| | | |
|---|---|---|
| 5,925,047 A | 7/1999 | Errico et al. |
| 5,935,130 A | 8/1999 | Kilpela et al. |
| 5,935,133 A | 8/1999 | Wagner et al. |
| 5,938,664 A | 8/1999 | Winquist et al. |
| 5,954,722 A | 9/1999 | Bono |
| 5,960,681 A | 10/1999 | Anderson et al. |
| 5,961,524 A | 10/1999 | Crombie |
| 5,964,769 A | 10/1999 | Wagner et al. |
| 5,968,046 A | 10/1999 | Castleman |
| 5,968,047 A | 10/1999 | Reed |
| 5,976,141 A | 11/1999 | Haag et al. |
| 6,016,727 A | 1/2000 | Morgan |
| 6,019,762 A | 2/2000 | Cole |
| 6,022,352 A | 2/2000 | Vandewalle |
| 6,053,921 A | 4/2000 | Wagner et al. |
| 6,096,040 A | 8/2000 | Esser |
| 6,102,951 A | 8/2000 | Sutter et al. |
| 6,129,730 A | 10/2000 | Bono et al. |
| 6,176,861 B1 | 1/2001 | Bernstein et al. |
| 6,183,475 B1 | 2/2001 | Lester et al. |
| 6,193,721 B1 | 2/2001 | Michelson |
| 6,206,881 B1 | 3/2001 | Frigg et al. |
| 6,214,049 B1 | 4/2001 | Gayer et al. |
| 6,228,085 B1 | 5/2001 | Theken et al. |
| 6,235,033 B1 | 5/2001 | Brace et al. |
| RE37,249 E | 6/2001 | Leibinger et al. |
| 6,258,092 B1 | 7/2001 | Dall |
| 6,273,889 B1 | 8/2001 | Richelsoph |
| 6,302,001 B1 | 10/2001 | Karle |
| 6,302,883 B1 | 10/2001 | Bono |
| 6,306,136 B1 | 10/2001 | Baccelli |
| 6,306,140 B1 | 10/2001 | Siddiqui |
| 6,309,393 B1 | 10/2001 | Tepic et al. |
| 6,322,562 B1 | 11/2001 | Wolter |
| 6,342,055 B1 | 1/2002 | Eisermann et al. |
| 6,355,041 B1 | 3/2002 | Martin |
| 6,355,043 B1 | 3/2002 | Adam |
| 6,358,250 B1 | 3/2002 | Orbay |
| 6,361,537 B1 | 3/2002 | Anderson |
| 6,364,885 B1 | 4/2002 | Kilpela et al. |
| 6,370,091 B1 | 4/2002 | Kuroda |
| 6,379,359 B1 | 4/2002 | Dahners |
| 6,386,808 B2 | 5/2002 | Fujii et al. |
| 6,391,030 B1 | 5/2002 | Wagner et al. |
| 6,413,259 B1 | 7/2002 | Lyons et al. |
| 6,428,542 B1 | 8/2002 | Michelson |
| 6,436,100 B1 | 8/2002 | Berger |
| 6,440,135 B2 | 8/2002 | Orbay et al. |
| 6,454,769 B2 | 9/2002 | Wagner et al. |
| 6,454,770 B1 | 9/2002 | Klaue |
| 6,468,278 B1 | 10/2002 | Muckter |
| 6,475,218 B2 | 11/2002 | Gournay et al. |
| 6,506,191 B1 | 1/2003 | Joos |
| 6,520,965 B2 | 2/2003 | Chervitz et al. |
| 6,524,238 B2 | 2/2003 | Velikaris et al. |
| 6,527,776 B1 | 3/2003 | Michelson |
| 6,558,387 B2 | 5/2003 | Errico et al. |
| 6,575,975 B2 | 6/2003 | Brace et al. |
| 6,595,993 B2 | 7/2003 | Donno et al. |
| 6,595,994 B2 | 7/2003 | Kilpela et al. |
| 6,605,090 B1 | 8/2003 | Trieu et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,682,531 B2 | 1/2004 | Winquist et al. |
| 6,682,533 B1 | 1/2004 | Dinsdale et al. |
| 6,684,741 B2 | 2/2004 | Blackston |
| 6,689,133 B2 | 2/2004 | Morrison et al. |
| 6,692,498 B1 | 2/2004 | Niiranen et al. |
| 6,692,581 B2 | 2/2004 | Tong et al. |
| 6,719,759 B2 | 4/2004 | Wagner et al. |
| 6,730,091 B1 | 5/2004 | Pfefferle et al. |
| 6,755,829 B1 | 6/2004 | Bono et al. |
| 6,767,351 B2 | 7/2004 | Orbay et al. |
| 6,780,186 B2 | 8/2004 | Errico et al. |
| 6,821,278 B2 | 11/2004 | Frigg et al. |
| 6,866,665 B2 | 3/2005 | Orbay |
| 6,893,443 B2 | 5/2005 | Frigg et al. |
| 6,893,444 B2 | 5/2005 | Orbay |
| 6,916,320 B2 | 7/2005 | Michelson |
| 6,945,975 B2 | 9/2005 | Dalton |
| 6,955,677 B2 * | 10/2005 | Dahners ............ A61B 17/8057 606/291 |
| 6,960,213 B2 | 11/2005 | Chervitz et al. |
| 6,969,390 B2 | 11/2005 | Michelson |
| 6,973,860 B2 | 12/2005 | Nish |
| 6,974,461 B1 | 12/2005 | Wolter |
| 6,979,334 B2 | 12/2005 | Dalton |
| 7,073,415 B2 | 7/2006 | Casutt et al. |
| 7,074,221 B2 | 7/2006 | Michelson |
| 7,128,744 B2 | 10/2006 | Weaver et al. |
| 7,172,593 B2 | 2/2007 | Trieu et al. |
| 7,179,260 B2 | 2/2007 | Gerlach et al. |
| 7,230,039 B2 | 6/2007 | Trieu et al. |
| 7,250,053 B2 | 7/2007 | Orbay |
| 7,250,054 B2 | 7/2007 | Allen et al. |
| 7,255,701 B2 | 8/2007 | Allen et al. |
| 7,282,053 B2 | 10/2007 | Orbay |
| 7,294,130 B2 | 11/2007 | Orbay |
| 7,341,589 B2 | 3/2008 | Weaver et al. |
| 7,419,714 B1 | 9/2008 | Magerl et al. |
| 7,637,928 B2 | 12/2009 | Fernandez |
| 7,695,472 B2 | 4/2010 | Young |
| 7,722,653 B2 | 5/2010 | Young et al. |
| 7,766,948 B1 | 8/2010 | Leung |
| 8,100,953 B2 | 1/2012 | White et al. |
| 8,105,367 B2 | 1/2012 | Austin et al. |
| 8,337,535 B2 | 12/2012 | White et al. |
| 8,512,385 B2 | 8/2013 | White et al. |
| 8,551,095 B2 * | 10/2013 | Fritzinger ........... A61B 17/8033 606/280 |
| 8,992,581 B2 | 3/2015 | Austin et al. |
| 9,987,062 B2 * | 6/2018 | Epperly ............. A61B 17/8057 |
| 10,390,866 B2 | 8/2019 | Baker et al. |
| 10,405,901 B2 | 9/2019 | Baker et al. |
| 11,534,213 B2 * | 12/2022 | Rapalo ............... A61B 17/8057 |
| 2001/0037112 A1 | 11/2001 | Brace et al. |
| 2001/0047174 A1 | 11/2001 | Donno et al. |
| 2002/0013587 A1 | 1/2002 | Winquist et al. |
| 2002/0045901 A1 | 4/2002 | Wagner et al. |
| 2002/0058940 A1 | 5/2002 | Frigg et al. |
| 2002/0058943 A1 | 5/2002 | Kilpela et al. |
| 2002/0115742 A1 | 8/2002 | Trieu et al. |
| 2002/0143338 A1 | 10/2002 | Orbay et al. |
| 2002/0161370 A1 | 10/2002 | Frigg et al. |
| 2003/0040749 A1 | 2/2003 | Grabowski et al. |
| 2003/0057590 A1 | 3/2003 | Loh Er et al. |
| 2003/0060827 A1 | 3/2003 | Coughln |
| 2003/0105462 A1 | 6/2003 | Haider |
| 2003/0183335 A1 | 10/2003 | Winniczek et al. |
| 2004/0010257 A1 | 1/2004 | Cachia et al. |
| 2004/0030342 A1 | 2/2004 | Trieu et al. |
| 2004/0044345 A1 | 3/2004 | DeMoss et al. |
| 2004/0059334 A1 | 3/2004 | Weaver et al. |
| 2004/0059335 A1 | 3/2004 | Weaver et al. |
| 2004/0073218 A1 | 4/2004 | Dahners |
| 2004/0087954 A1 | 5/2004 | Allen et al. |
| 2004/0097942 A1 | 5/2004 | Allen et al. |
| 2004/0122430 A1 | 6/2004 | Hansson et al. |
| 2004/0138666 A1 | 7/2004 | Molz et al. |
| 2004/0181228 A1 | 9/2004 | Wagner et al. |
| 2004/0186477 A1 | 9/2004 | Winquist et al. |
| 2004/0199169 A1 | 10/2004 | Koons et al. |
| 2004/0213645 A1 | 10/2004 | Kovac |
| 2004/0215195 A1 | 10/2004 | Shipp et al. |
| 2004/0220570 A1 | 11/2004 | Frigg |
| 2004/0236332 A1 | 11/2004 | Frigg |
| 2004/0260306 A1 | 12/2004 | Fallin et al. |
| 2005/0010220 A1 | 1/2005 | Casutt et al. |
| 2005/0010226 A1 | 1/2005 | Grady et al. |
| 2005/0027298 A1 | 2/2005 | Michelson |
| 2005/0043736 A1 | 2/2005 | Mathieu et al. |
| 2005/0049593 A1 | 3/2005 | Duong et al. |
| 2005/0049594 A1 | 3/2005 | Wack et al. |

(56) References Cited

U.S. PATENT DOCUMENTS

| | | |
|---|---|---|
| 2005/0070904 A1 | 3/2005 | Gerlach et al. |
| 2005/0080421 A1 | 4/2005 | Weaver et al. |
| 2005/0107796 A1 | 5/2005 | Gerlach et al. |
| 2005/0137597 A1 | 6/2005 | Butler et al. |
| 2005/0149026 A1 | 7/2005 | Buller et al. |
| 2005/0165400 A1 | 7/2005 | Fernandez |
| 2005/0192580 A1 | 9/2005 | Dalton |
| 2005/0222570 A1 | 10/2005 | Jackson |
| 2005/0234457 A1 | 10/2005 | James et al. |
| 2005/0261688 A1 | 11/2005 | Grady et al. |
| 2005/0277937 A1 | 12/2005 | Leung et al. |
| 2005/0283154 A1 | 12/2005 | Orbay et al. |
| 2006/0004361 A1 | 1/2006 | Hayeck et al. |
| 2006/0009770 A1 | 1/2006 | Speirs et al. |
| 2006/0009771 A1 | 1/2006 | Orbay et al. |
| 2006/0095040 A1 | 5/2006 | Schlienger et al. |
| 2006/0116678 A1 | 6/2006 | Impellizzeri |
| 2006/0122602 A1 | 6/2006 | Konieczynski et al. |
| 2006/0129148 A1 | 6/2006 | Simmons et al. |
| 2006/0129151 A1 | 6/2006 | Allen et al. |
| 2006/0149265 A1 | 7/2006 | James et al. |
| 2006/0165400 A1 | 7/2006 | Spencer |
| 2006/0167464 A1 | 7/2006 | Allen et al. |
| 2006/0200147 A1 | 9/2006 | Ensign et al. |
| 2006/0235400 A1 | 10/2006 | Schneider |
| 2006/0235410 A1 | 10/2006 | Ralph et al. |
| 2006/0259039 A1 | 11/2006 | Pitkanen et al. |
| 2007/0010817 A1 | 1/2007 | de Coninck |
| 2007/0043366 A1 | 2/2007 | Pfefferle et al. |
| 2007/0093836 A1 | 4/2007 | Derouet |
| 2007/0161995 A1 | 7/2007 | Trautwein et al. |
| 2007/0162016 A1 | 7/2007 | Matityahu |
| 2007/0162020 A1 | 7/2007 | Gerlach et al. |
| 2007/0185488 A1 | 8/2007 | Pohjonen et al. |
| 2007/0213828 A1 | 9/2007 | Trieu et al. |
| 2007/0233106 A1 | 10/2007 | Horan et al. |
| 2007/0260244 A1 | 11/2007 | Wolter |
| 2007/0270691 A1 | 11/2007 | Bailey et al. |
| 2007/0270832 A1 | 11/2007 | Moore |
| 2007/0270833 A1 | 11/2007 | Bonutti et al. |
| 2007/0276383 A1 | 11/2007 | Rayhack |
| 2008/0021474 A1 | 1/2008 | Bonutti et al. |
| 2008/0039845 A1 | 2/2008 | Bonutti et al. |
| 2008/0086129 A1 | 4/2008 | Lindemann et al. |
| 2008/0140130 A1 | 6/2008 | Chan et al. |
| 2008/0154367 A1 | 6/2008 | Justis et al. |
| 2008/0154368 A1 | 6/2008 | Justis et al. |
| 2008/0154373 A1 | 6/2008 | Protopsaltis et al. |
| 2008/0167717 A9 | 7/2008 | Trieu et al. |
| 2008/0200955 A1 | 8/2008 | Tepic |
| 2008/0208259 A1 | 8/2008 | Gilbert et al. |
| 2008/0234677 A1 | 9/2008 | Dahners et al. |
| 2008/0234748 A1 | 9/2008 | Wallenstein et al. |
| 2008/0234751 A1 | 9/2008 | McClintock |
| 2008/0300637 A1 | 12/2008 | Austin et al. |
| 2009/0024161 A1 | 1/2009 | Bonutti et al. |
| 2009/0076553 A1 | 3/2009 | Wolter |
| 2009/0088807 A1 | 4/2009 | Castaneda et al. |
| 2009/0143824 A1 | 6/2009 | Austin et al. |
| 2009/0149888 A1 | 6/2009 | Abdelgany |
| 2009/0192549 A1 | 7/2009 | Sanders et al. |
| 2009/0312803 A1 | 12/2009 | Austin et al. |
| 2010/0160973 A1 | 6/2010 | Leung |
| 2010/0256686 A1 | 10/2010 | Fisher et al. |
| 2010/0312286 A1 | 12/2010 | Dell'Oca |
| 2011/0015681 A1 | 1/2011 | Elsbury |
| 2011/0071572 A1 | 3/2011 | Sixto et al. |
| 2011/0264149 A1 | 10/2011 | Pappalardo et al. |
| 2012/0059425 A1 | 3/2012 | Biedermann |
| 2012/0083847 A1 | 4/2012 | Huebner et al. |
| 2012/0136396 A1 | 5/2012 | Baker et al. |
| 2012/0143193 A1 | 6/2012 | Hulliger |
| 2012/0265253 A1 | 10/2012 | Conley et al. |
| 2012/0323284 A1 | 12/2012 | Baker et al. |
| 2013/0165977 A1 | 6/2013 | Biedermann et al. |
| 2014/0316473 A1 | 10/2014 | Pfeiffer et al. |
| 2015/0257802 A1* | 9/2015 | Wolf ................ A61B 17/8014 606/291 |
| 2018/0250049 A1 | 9/2018 | Baker et al. |

FOREIGN PATENT DOCUMENTS

| | | |
|---|---|---|
| CA | 2408327 C | 3/2001 |
| CA | 2536960 A1 | 3/2005 |
| CH | 611147 A5 | 5/1979 |
| CN | 1380043 A | 11/2002 |
| DE | 2602900 C3 | 4/1979 |
| DE | 3513600 A1 | 10/1986 |
| DE | 3804749 A1 | 3/1989 |
| DE | 3832343 A1 | 3/1990 |
| DE | 4341980 A1 | 6/1995 |
| DE | 4343117 A1 | 6/1995 |
| DE | 4438261 C1 | 9/1995 |
| DE | 4438264 C2 | 11/1996 |
| DE | 19629011 A1 | 1/1998 |
| DE | 102005015496 A1 | 11/2006 |
| DE | 102005042766 A1 | 1/2007 |
| DE | 19858889 B4 | 8/2008 |
| EP | 0201024 A1 | 11/1986 |
| EP | 0207884 A2 | 1/1987 |
| EP | 0274713 A1 | 7/1988 |
| EP | 0355035 A2 | 2/1990 |
| EP | 0468192 A3 | 4/1992 |
| EP | 0486762 B1 | 5/1995 |
| EP | 0530585 B1 | 12/1996 |
| EP | 0760632 A1 | 3/1997 |
| EP | 0799124 B1 | 8/2001 |
| EP | 0828459 B1 | 9/2003 |
| EP | 1649819 A1 | 4/2006 |
| EP | 1813292 A1 | 8/2007 |
| EP | 1857073 A1 | 11/2007 |
| FR | 2480106 A1 | 10/1981 |
| FR | 2667913 A1 | 4/1992 |
| FR | 2698261 B1 | 3/1995 |
| FR | 2739151 B1 | 11/1997 |
| FR | 2757370 B1 | 6/1998 |
| FR | 2963396 A1 | 2/2012 |
| GB | 580571 A | 9/1946 |
| GB | 2521346 A | 6/2015 |
| JP | 2003509107 A | 3/2003 |
| RU | 2234878 C2 | 8/2004 |
| SU | 1279626 A1 | 12/1986 |
| TW | 477687 B | 3/2002 |
| WO | WO1989004150 A1 | 5/1989 |
| WO | WO1990007304 A1 | 7/1990 |
| WO | WO1996009014 A1 | 3/1996 |
| WO | WO1996019336 A1 | 6/1996 |
| WO | WO1996025892 A1 | 8/1996 |
| WO | WO1996029948 A1 | 10/1996 |
| WO | WO1997009000 A1 | 3/1997 |
| WO | WO1998034553 A1 | 8/1998 |
| WO | WO1998034556 A1 | 8/1998 |
| WO | WO1999005968 A1 | 2/1999 |
| WO | WO1999025266 A1 | 5/1999 |
| WO | WO1999061081 A1 | 12/1999 |
| WO | WO2000018309 A1 | 4/2000 |
| WO | WO2000019264 A1 | 4/2000 |
| WO | WO2000036984 A1 | 6/2000 |
| WO | WO2000053110 A1 | 9/2000 |
| WO | WO2000053111 A1 | 9/2000 |
| WO | WO2000066012 A1 | 11/2000 |
| WO | WO2001019267 A1 | 3/2001 |
| WO | WO2001019268 A1 | 3/2001 |
| WO | WO2001019264 A1 | 8/2001 |
| WO | WO2001078615 A1 | 10/2001 |
| WO | WO2001091660 A1 | 12/2001 |
| WO | WO2002000127 A1 | 1/2002 |
| WO | WO2002058574 A2 | 8/2002 |
| WO | WO2002068009 A2 | 9/2002 |
| WO | WO2002034159 A3 | 11/2002 |
| WO | WO2002096309 A1 | 12/2002 |
| WO | WO2003006210 A1 | 1/2003 |
| WO | WO2003106110 A1 | 12/2003 |
| WO | WO2004032726 A2 | 4/2004 |

(56) References Cited

FOREIGN PATENT DOCUMENTS

| WO | WO2004032751 A3 | 5/2004 |
|---|---|---|
| WO | WO2004086990 A1 | 10/2004 |
| WO | WO2004089233 A1 | 10/2004 |
| WO | 2004/107957 A2 | 12/2004 |
| WO | WO2005018471 A1 | 3/2005 |
| WO | WO2005018472 A1 | 3/2005 |
| WO | WO2005032386 A1 | 4/2005 |
| WO | WO2005034722 A1 | 4/2005 |
| WO | WO2005079685 A1 | 9/2005 |
| WO | WO2005062902 A3 | 12/2005 |
| WO | WO2006007965 A1 | 1/2006 |
| WO | WO2006039636 A2 | 4/2006 |
| WO | WO2006068775 A2 | 6/2006 |
| WO | WO2007014279 A2 | 2/2007 |
| WO | WO2007025520 A1 | 3/2007 |
| WO | WO2007041686 A1 | 4/2007 |
| WO | WO2007014192 A3 | 5/2007 |
| WO | WO2007092869 A2 | 8/2007 |
| WO | WO2007130840 A1 | 11/2007 |
| WO | WO200802213 A1 | 1/2008 |
| WO | WO2008033742 A1 | 3/2008 |
| WO | WO2008064211 A1 | 5/2008 |
| WO | WO2008077137 A1 | 6/2008 |
| WO | WO2008079846 A1 | 7/2008 |
| WO | WO2008079864 A1 | 7/2008 |
| WO | WO2008116203 A3 | 12/2008 |
| WO | WO2009029908 A1 | 3/2009 |
| WO | WO2013/059090 A1 | 4/2013 |

OTHER PUBLICATIONS

Wolter, D., et al., "Universal Internal Titanium Fixation Device," Trauma Berufskrankh (1999) 1:307-309, Springer-Verlag 1999, Certified English Translation Thereof.

Bohmer, G., et al., "Ti Fix® Angularly Stable Condylar Plate," Trauma Berufskrankh (1999) 1 :351-355, Springer-Verlag 1999, Certified English Translation Thereof.

Kranz, H.-W., et al., "Internal Titanium Fixation of Tibial Pseudarthrosis, Malalignment, and Fractures," Trauma Berufskrankh (1999) 1 :356-360, Springer-Verlag 1999, Certified English Translation Thereof.

Fuchs, S., et al., "Clinical Experiences with a New Internal Titanium Fixator for Ventral Spondylodesis of the Cervical Spine, " Trauma Berufskrankh (1999) 1 :382-386, Springer-Verlag 1999, Certified English Translation Thereof.

Jurgens, C., et al., "Special Indications for the Application of the Fixed Angle Internal Fixation in Femur Fractures," Trauma Berufskrankh (1999) 1 :387,391, Springer-Verlag 1999, Certified English Translation Thereof.

Wolter, D., et al., "Titanium Internal Fixator for the Tibia," Trauma Berufskrankh, Mar. 2001 (Supp 2): S156-S161, Springer-Verlag 2001, Certified English Translation Thereof.

Fuchs, S., et al., "Titanium Fixative Plate System with Multidirectional Angular Stability in the Lower Leg and Foot," Trauma Berufskrankh, Mar. 2001 (Suppl 4): S447-S453, Springer-Verlag 2001, Certified English Translation Thereof.

Smith & Nephew Brochure entitled 'Surgical Technique PERI-LOC VLP Variable-Angle Locked Plating System,' pp. 1-32 (Nov. 2007).

Smith & Nephew Brochure entitled 'PERI-LOC VLP Variable-Angle Locked Plating System Distal Tibia Locking Plates,' 04 pages (Oct. 2007).

Smith & Nephew Brochure entitled 'PERI-LOC VLP Variable-Angle Locked Plating System Distal Fibula Locking Plates,' 04 pages (Oct. 2007).

Smith & Nephew Brochure entitled 'PERI-LOC VLP Variable-Angle Locked Plating System Proximal Tibia Locking Plates,' 04 pages (Oct. 2007).

Smith & Nephew Brochure entitled 'PERI-LOC VLP Variable-Angle Locked Plating System Proximal Tibia Variable-Angle Locking Plates,' 04 pages (Nov. 2007).

Smith & Nephew Brochure entitled 'PERI-LOC VLP Variable-Angle Locked Plating System Improved Torsional Fatigue Properties with Thin Locked Versus Non-Locked Plate Constructs for Fixation of Simulated Osteoporotic Distal Fibula Fractures,' 04 pages (Nov. 2007).

Winkelstabilitat, litos Unidirectional locking screw technology, Jan. 15, 2008, 5 pages http://www.litos.com/pages/winkelsta bilitaet e.html.

"SMARTLock Locking Screw Technology," http://www.stryker.com/microimplants/products/cmf smartlock.phn, Mar. 14, 2004.

"Fracture and Dislocation Compendium," Orthopaedic Trauma Association Committee for Coding and Classification, Journal of Orthopaedic Trauma, vol. 10, Suppl.,jp, v = ix, 1996.

NCB® Proximal Humerus Plating System, Surgical Technique, Zimmer, Inc. 2005.

Zimmer® NCB® Plating System, Zimmer, Inc. 2006.

NCB® Distal Femoral Plating System, Surgical Technique, Zimmer, Inc. 2005.

New Trauma Products from AO Development, News—No. 1, 2007.

"Polyax Wide Angle Freedom Surgical Technique Distal Femoral Locked Playing System," DePuy International Ltd., http://www/rcsed .ac.u k/fellows/lva nrensbu rg/ classification/su rgtech/depuy (2005).

DePuy Orthopaedics, Inc., "Surgical Technique Distal Femoral Locked Plating System," Polyax Wide Angle Freedom (2005).

Decision of Rejection for Japanese Application No. 2008-0524048, dated Oct. 30, 2011.

Office Action for U.S. Appl. No. 11/996,795, dated Nov. 21, 2012.

\* cited by examiner

BONE PLATE

CROSS-REFERENCE TO RELATED APPLICATIONS

This application is a continuation of U.S. application Ser. No. 17/222,503, filed Apr. 5, 2021, now U.S. Pat. No. 11,534,213, issued Dec. 27, 2022, which application is a continuation of U.S. application Ser. No. 15/758,207, filed Mar. 7, 2018, now U.S. Pat. No. 10,993,750, issued May 4, 2021, which is a United States National Phase filing of International Application No. PCT/US2016/051864, filed Sep. 15, 2016, which claims the benefit of U.S. Provisional Application No. 62/220,562, filed on Sep. 18, 2015. The disclosure of each application is incorporated by reference in its entirety.

BACKGROUND

Embodiments of the present invention generally relate to variable angle holes in bone plates. More particularly, but not exclusively, embodiments of the present invention relate to variable angle holes in bone plates that are structured to facilitate the formation of axial compression or tension in a bone.

The treatment of at least certain types of bone fractures often includes securing a bone plate against the bone and across at least a portion of the fracture. Such bone plates, which can at least improve fracture stability, can be transversally compressed against the bone through the use of one or more fixation elements such as, for example, screws, that enter into the bone at relatively precise locations along the bone plate. Yet, axial compression or distraction of bones typically requires an additional, separate plate that is also attached to the bone by fixation elements. However, such an additional, separate plate is often generally bulky in size and occupies additional space in the surgical tray. Further, the apertures in such additional plates are often sized or structured in a manner that can compromise the strength of the bone plate.

BRIEF SUMMARY

Certain embodiments of the invention may include a bone plate configured to receive the insertion of one or more fixation devices that secure the bone plate to one or more bone segments. The bone plate includes a first end and a second end and axially extends between the first and second ends along a central longitudinal axis of the bone plate and at least one variable angle hole. The at least one variable angle hole includes a wedge wall and at least one axial offset recess, the axial offset recess being elongated along at least the central longitudinal axis and sized to receive insertion of at least a portion of one of the fixation elements at a location in the at least one variable angle hole at which a central axis of the received fixation element is at least axially offset by an offset distance from a central longitudinal axis of the at least one variable angle hole. The wedge wall can have a shape that is configured to be engaged by at least a portion of the fixation element to axially displace at least one of the bone plate and the received bone segment in a direction that decreases the offset distance between the central axis of the received fixation element and the central longitudinal axis of the at least one variable angle hole.

Additionally, certain embodiments of the invention may include an apparatus that includes a bone plate having a top side and a bottom side and a variable angle hole positioned along the bone plate. The variable angle hole can have a wedge wall that inwardly extends from top side of the bone plate toward a central axis of the variable angle hole. The variable angle hole can be sized to receive insertion of a fixation element at a location at which a central longitudinal axis of the fixation element is axially offset from the central axis by an offset distance at least when the fixation element is initially driven into a bone at least in a transverse direction. Further, the wedge wall can be configured to be engaged by a portion of the fixation element in a manner that axially displaces at least one of the bone plate and the fixation element in a direction that reduces the offset distance.

Certain embodiments of the invention may also include a bone plate configured to receive insertion of one or more fixation devices that secure the bone plate to one or more bone segments. The bone plate includes a top surface and a bottom surface on opposing sides of the bone plate, the bone plate axially extending between a first end and a second end of the bone plate along a central longitudinal axis of the bone plate. The bone plate further includes at least one fixed-variable angle hole that extends through the bone plate. The at least one fixed-variable angle hole has an inner wall that defines an orifice. Additionally, the at least one fixed-variable angle includes a plurality of recesses that are sized and shaped to receive insertion of at least a portion of a fixation element of the one or more fixation elements into the at least one fixed-variable angle hole in a plurality of orientations that are non-parallel to a central axis of the at least one fixed-variable angle hole. Further, the at least one fixed-variable angle hole includes a plurality of projections that inwardly extend from the inner wall that are structured to lockingly engage a threaded portion of a head portion of the received fixation element when the received fixation element is positioned in the fixed-variable angle hole at an orientation that is generally parallel to the central axis of the at least one fixed-variable angle hole.

BRIEF DESCRIPTION OF THE DRAWINGS

The description herein makes reference to the accompanying figures wherein like reference numerals refer to like parts throughout the several views.

Figure 1A:
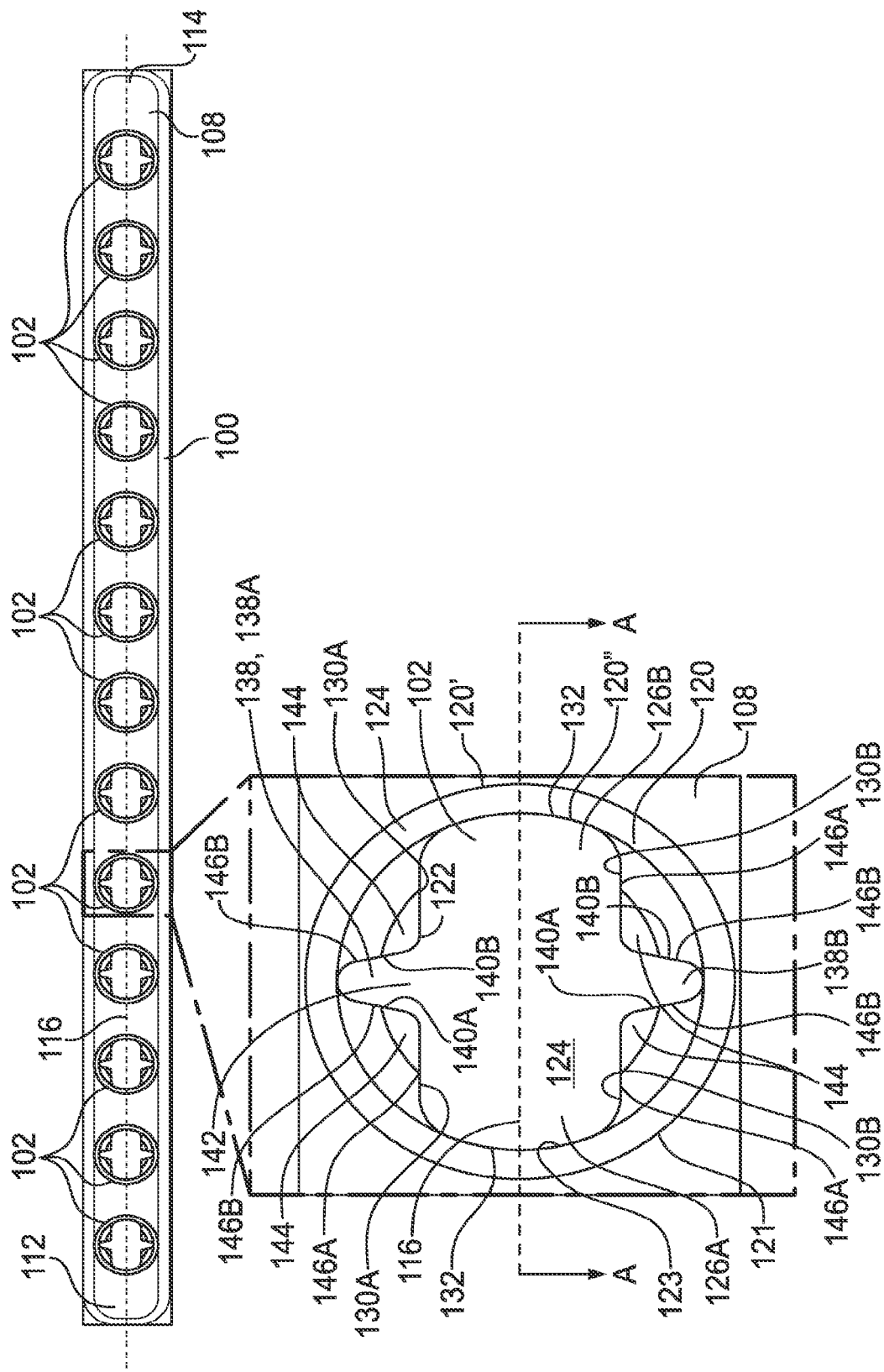
FIG. 1A illustrates a top view of a bone plate having variable angle locking holes structured to at least assist in facilitating axial compression and/or distraction of a bone fracture site.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DESCRIPTION OF THE ILLUSTRATED EMBODIMENTS

Certain terminology is used in the foregoing description for convenience and is not intended to be limiting. Words such as "upper," "lower," "top," "bottom," "first," and "second" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

Figure 1B:
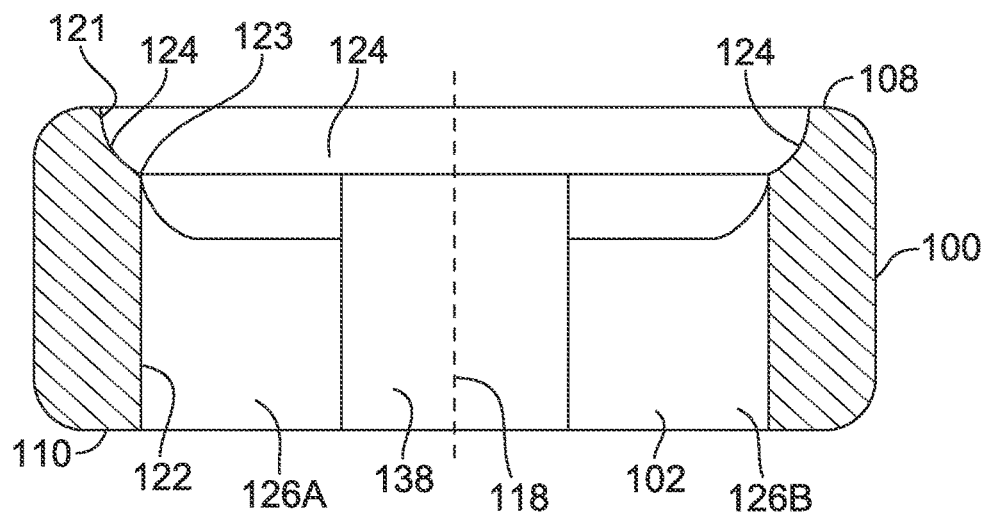
FIG. 1B illustrates a cross sectional view of a variable angle locking hole taken along line A-A of FIG. 1A.
Figure 2:
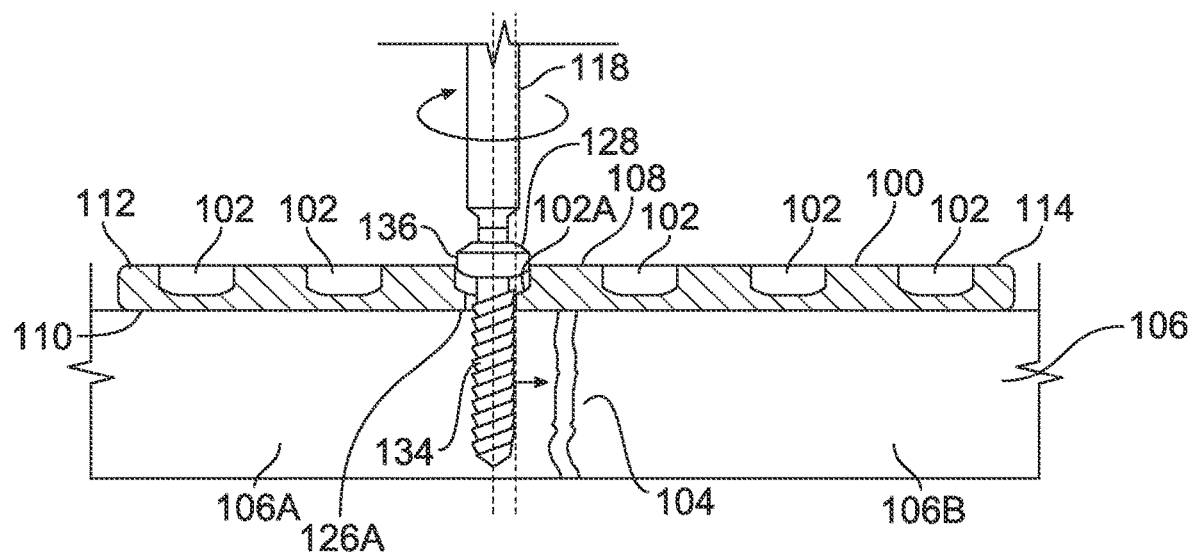
FIG. 2 illustrates exemplary fixation of a bone plate to a fracture site along a bone using a fixation element that is positioned at an offset location relative to a central axis of a receiving variable angle locking hole of the bone plate.

FIGS. 1A and 1B illustrate a top view and a cross sectional view, respectively, of an exemplary bone plate 100 having a plurality of variable angle locking holes 102 that are structured to at least assist in facilitating axial compression of a fracture site 104 (FIG. 2) and/or distraction of a bone(s) 106a, 106b (FIG. 2). The bone plate 100 can include opposite top and bottom sides 108, 110, as well as opposite first and second ends 112, 114. Further, the bone plate 100 can have a variety of different shapes and sizes. For example, according to certain embodiments, one or more sections of the bone plate 100 can have contours or curves that generally correspond to similar contours or curves of a portion of the bone 106 against which the bottom side 110 of the bone plate 100 can abut or otherwise be located at an adjacent position. In the illustrated embodiment, the bone plate 100 can extend between the first and second ends 112, 114 along a central longitudinal axis 116 of the bone plate 100. Further, the bone plate 100 can be constructed from a variety of materials, including, for example, stainless steel, titanium, polymers, and/or ceramics, among other materials.

The bone plate 100 can include one or more variable angle locking holes 102, among other static locking or non-locking holes and/or apertures in the bone plate 100. At least a portion of the variable angle locking holes 102 can extend from the top side 108 to the bottom side 110 of the bone plate 100 along a central axis 118 of each of the variable angle locking holes 102 as shown, for example, in FIG. 1B. As shown in FIGS. 1A and 1B, the variable angle locking holes 102 can include one or more ramps or wedge walls 120 that extend around at least a portion of an outer periphery of the variable angle locking hole 102 along the top side 108 of and into the bone plate 100. As discussed below, the wedge wall 120 can be configured to provide a wedge or ramp effect on at least the bone plate 100 when engaged by a fixation element such as, for example, a screw that provides a force to axially displace, deform, and/or compress the bone plate 100 at least in a direction that can be generally parallel to the central longitudinal axis 116 of the bone plate 100 and/or the adjacent bone 106. Further, according to certain embodiments, in addition to, or in lieu of, displacing, deforming, and/or compressing the bone plate 100, the wedge wall 120 can be configured to, when operably engaged with a fixation element, axially displace, influence an axial position and/or assist in providing an axial compressive force against one or more bones 106 or bone segments 106a, 106b such as, for example, in connection with bring/retaining bones to a particular location for fracture repair or bone distraction.

According to the embodiment illustrated in FIGS. 1A and 1B, the variable angle locking hole 102 can include an inner wall 122 that generally defines an orifice 124 of the variable angle locking hole 102. At least a portion of the orifice 124 generally extends about the central axis 118 of the variable angle locking hole 102 extending through the bone plate 100. The orifice 124 can have a variety of shapes and sizes, and can be symmetrical or asymmetrical about the central axis 118.

Referring to FIGS. 1A and 1B, the orifice 124 can include a first axial offset recess 126a and a second axial offset recess 126b, the first and second axial offset recesses 126a, 126b being located on opposite sides of the orifice 124. Further, according to the illustrated embodiment, the first and second axial offset recesses 126a, 126b can have elongated shapes that extend axially generally along the central axis 118. Moreover, the inner wall 122 along both the first and second axial offset recesses 126a, 126b can include a first wall segment 130a and an opposing second wall segment 130b that are interconnected by an end wall segment 132. Further, according to certain embodiments, the central longitudinal axis 116 of the bone plate 100 can extend through a portion of the end wall segment 132 such as, for example, through a middle section or region of the end wall segment 132. Referring to FIG. 1A and FIG. 4A, in some embodiments, the first and second wall segments 130a, 130b can be arranged generally parallel to one another. Further, according to the illustrated embodiment, the first and second wall segments 130a, 130b can be arranged generally parallel to the central longitudinal axis 116. Additionally, the first and second wall segments 130a, 130b can be separated from one another by a distance that is approximately equal to or larger than a corresponding size, such as a diameter, of at least a threaded or non-threaded shank portion 134 of the fixation element 128 that is positioned adjacent to a head portion 136 of the fixation element 128.

Referring to FIG. 1A, according to certain embodiments, the orifice 124 can also include one or more angular positioning recesses 138a, 138b, or static angular positioning recesses, that is/are positioned about the orifice 124 between the first and second axial offset recesses 126a, 126b. For example, according to the embodiment illustrated in FIG. 1A, the orifice 124 can include a first angular positioning recess 138a and a second angular positioning recess 138b, the first and second angular positioning recesses 138a, 138b being positioned at or around a mid-section of the inner wall 122 between the first and second axial offset recesses 126a, 126b and on opposite sides of the central longitudinal axis 116. The angular positioning recesses 138a, 138b can be configured to accommodate insertion of the fixation element 128 into the orifice 124 at certain angles relative to the central axis 118 of the orifice 124. Thus, the angular positioning recesses 138a, 138b can extend the width or size of the orifice 124 in at least certain directions so that a fixation element 128 can be inserted into the variable angle locking hole 102 from the top side of the bone plate 100 and through the variable angle locking hole 102 at the bottom side 110 of the bone plate 100 at certain angles that are non-parallel to the central axis 118 of the variable angle locking hole 102.

As shown in FIG. 1A, according to certain embodiments, the angular positioning recesses 138a, 138b can include a pair of converging sidewalls 140a, 140b. Further, the width of the distance between the sidewalls 140a, 140b of the angular positioning recesses 138a, 138b can generally be less than the distance between the first and second wall segments 130a, 130b of each of the first and second axial offset recesses 126a, 126b. For example, according to the illustrated embodiment, the largest distance between the sidewalls 140a, 140b of the angular positioning recesses 138a, 138b such as, for example, at a mouth portion 142 of the angular positioning recesses 138a, 138b at which the sidewalls 140a, 140b can begin to extend in converging directions, can be smaller than the distance between opposing first and second wall segments 130a, 130b of the orifice 124.

The first and second axial offset recesses 126a, 126b can be separated from adjacent angular positioning recesses 138a, 138b by one or more tabs 144. According to the illustrated embodiment, a side 146a of one or more of the tabs 144 can be generally defined by either the first or second wall segment 130a, 130b, and another side 146b of the one or more tabs 144 can be defined by one of the sidewalls 140a, 140b of the adjacent angular positioning recess 138. The tabs 144 can be sized such that, at least when a portion of the fixation element 128 extends into the variable angle locking hole 102, a portion of the fixation element 128 lockingly engages one or more of the tabs 144. For example, according to certain embodiments, a head portion 136 of the fixation element 128, or another portion of the fixation element 128 that is in proximity to the head portion 136, can be threadingly engaged with or mate with corresponding portions of one or more sides 146a, 146b of one or more of the tabs 144, including, but not limited to, threads or protrusions that can be positioned along one or more sides of sides 146a, 146b of the tabs 144. Further, the tabs 144 can be sized to provide interference that prevents at least a portion of the fixation element 128 such as, for example, the head portion 136, from being pulled entirely through the orifice 124.

According to certain embodiments, at least a portion of the wedge wall 120 that can engage the fixation element 128 can have a shape and/or orientation that is arranged non-parallel and non-perpendicular to the central axis 118 of the variable angle locking hole 102. For example, referring to FIG. 1B, according to certain embodiments, the wedge wall 120 can include an outer end 121 that extends inwardly toward a second, inner end 123, the outer end 121 being in closer proximity than the inner end 123 to the top side 108 of the bone plate 100, and the inner end 123 being in closer proximity than the outer end 121 to the central longitudinal axis 116 of the bone plate 100. For example, according to certain embodiments, the wedge wall 120 can be one or more of an angled, tapered, inclined and/or curved surface that extends generally inwardly and/or downwardly into the bone plate 100 from or around the top side 108 of the bone plate 100. According to certain embodiments, an additional first secondary wedge wall 120' can be provided by a chamfer or transition surface between the top side 108 of the bone plate 100 and the wedge wall 120, and/or a second secondary wedge wall 120" that extends as a transition between the wedge wall 120 and the inner wall 122 of the bone plate 100.

Figure 3:
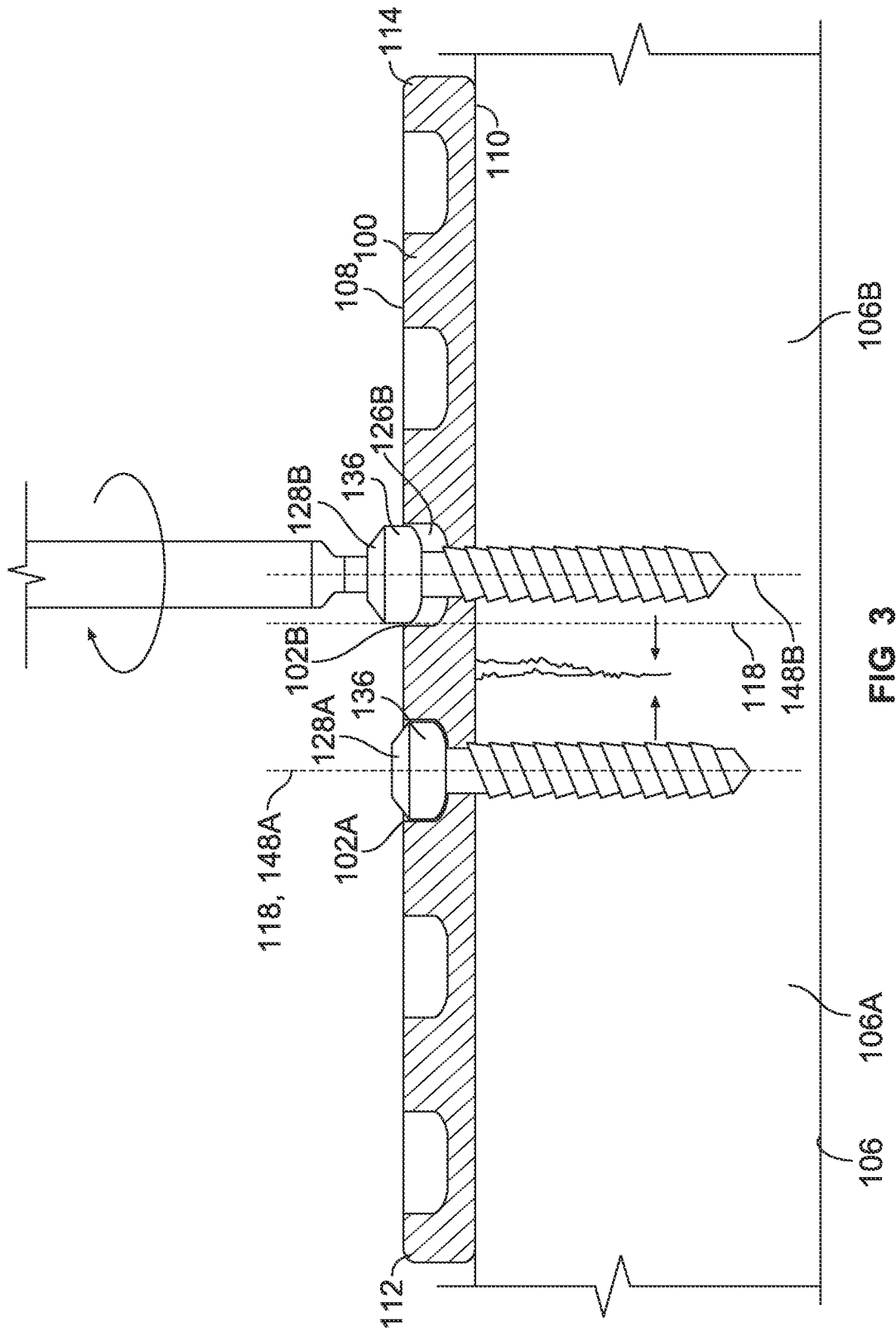
FIG. 3 illustrates exemplary axial compression of a bone in which multiple fixation elements are driven into the bone at offset locations in variable angle locking holes of a bone plate.
Figure 4:
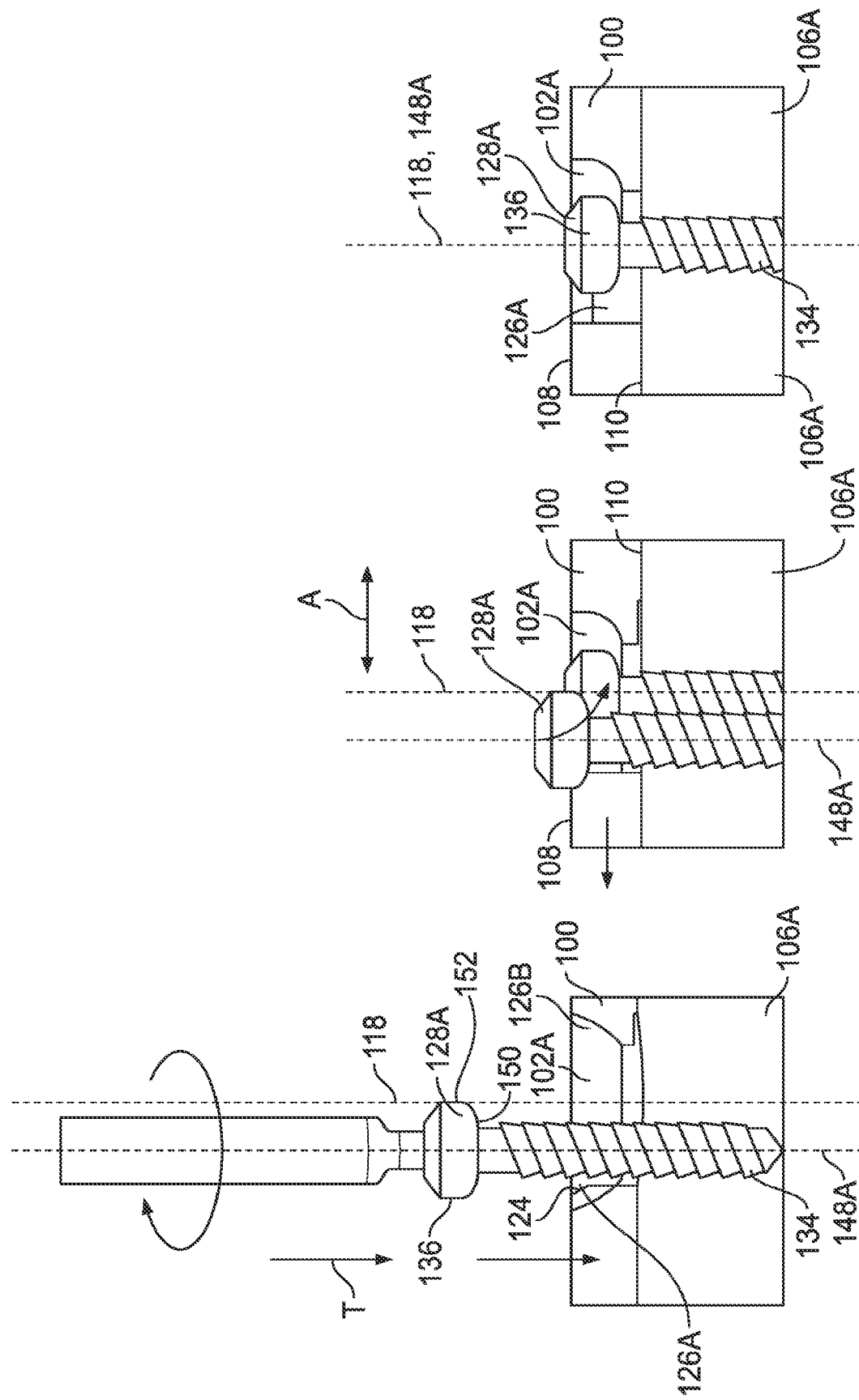
FIGS. 4A-4C illustrate different stages of engagement between a fixation element that is being driven into a bone and a variable angle locking hole of a bone plate that is configured to at least assist in facilitating axial compression and/or distraction of a bone fracture site.

FIGS. 2 and 4A illustrate an example of a first fixation element 128a being driven generally in at least a transverse direction (as indicated by the "T" direction in FIG. 4A) through a first axial offset recess 126a of a variable angle locking hole 102a of a bone plate 100 and into a bone 106 such as, for example, a bone 106 having a fracture site 104 between a first bone segment 106a and a second bone segment 106b. For purposes of illustrating the examples depicted in FIGS. 2-4C, at least a portion of the bone plate 100 can already be secured to the first and second bone segments 106a, 106b via the implantation of other fixation elements (not shown) through other holes and/or other apertures in the bone plate 100. For example, according to certain embodiments, fixation elements can have previously been at least partially driven into the first and second bone segments 106a, 106b through other holes and/or apertures at or around opposing first and second ends 112, 114 of the bone plate 100 prior to the implantation of the first and second fixation elements 128a, 128b (FIGS. 2-4C) into the bone 106.

As illustrated in FIGS. 2-4B, and as discussed above, according to the illustrated embodiment, the first and second axial offset recesses 126a, 126b are sized to accommodate insertion of at least a portion of the first fixation element 128a at locations that are offset from the central axis 118a of the variable angle locking hole 102a. For example, referring to FIGS. 2 and 4A, in the illustrated embodiment, the first fixation element 128a can, as the fixation element 128a is at least initially being driven into the first bone segment 106a, be positioned at a location relative to the first axial offset recess 126a such that the central longitudinal axis 148a of the first fixation element 128a is at least initially offset from and non-intersecting with the central axis 118a of the variable angle locking hole 102a. Further, in the illustrated embodiment, in at least certain embodiments, at least the first axial offset recess 126a can be sized and shaped such that the central longitudinal axis 148a of the first fixation element 128a that extends into the first axial offset recess 126a can be arranged generally parallel to the central axis 118a of the variable angle locking hole 102. However, according to other implantations or embodiments, the central longitudinal axis 148a of the first fixation element 128a can be arranged non-parallel to the central longitudinal axis 148a as the first fixation element 128a is at least initially driven into the first bone segment 106a.

As the first fixation element 128a in the illustrated embodiment proceeds to be driven into the first bone segment 106a, at least a portion of the head portion 136 of the first fixation element 128a can come into contact with the wedge wall 120 of the variable angle locking hole 102a, as illustrated in FIGS. 2 and 4B. According to certain embodiments, a bottom surface 150 and/or edge surface 152 of the head portion 136 of the first fixation element 128a can have a shape that facilitates axial displacement, such as sliding, and/or deformation of at least a portion of the bone plate 100 in an axial direction (as indicated by the "A" direction in FIG. 4B) and/or facilitate axial displacement, positioning, and/or assist in providing an axial compressive force against the bone 106 or bone segment(s) 106a, 106b as the first fixation element 128a continues to be driven at least in a transverse direction into the first bone segment 106a. For example, according to certain embodiments, the bottom and/or edge surfaces 150, 152 of the head portion 136 can have a tapered or inclined shape that can generally mate with the shape of at least a portion of the wedge wall 120 of the variable angle locking hole 102a so as to facilitate, for example, axial displacement of the bone plate 100 and/or bone segment 106a, and/or facilitate a compressive force against the fracture site 104.

According to such an embodiment, as the first fixation element 128a, and more specifically the head portion 136 of the first fixation element 128a engages the wedge wall 120 of the variable angle locking hole 102a, the interaction between the first fixation element 128a and the wedge wall 120 can result in a pulling or pushing force being exerted on the bone plate 100 and/or bone 106 or bone segment(s) 106a, 106b that seeks to axially displace the bone plate 100 and/or bone 106 or bone segment(s) 106a, 106b in a manner that at least attempts to bring the central axis 118 of the variable angle locking hole 102a into closer proximity to or alignment with the central longitudinal axis 148a of the first fixation element 128a. For example, according to the embodiment illustrated in FIG. 2, the first fixation element 128a can be at least initially positioned in the first axial offset recess 126a of the variable angle locking hole 102a such that the head portion 136 of the first fixation element 128a can contact a portion of the wedge wall 120 that is in closer proximity to the first end 112 of the bone plate 100 than other portions of the wedge wall 120. Accordingly, as the first fixation element 128a continues to be driven into the first bone segment 106a, engagement between the head portion 136 of the first fixation element 128a and the wedge wall 120 can result in a force that attempts to at least axially displace the bone plate 100 generally in the direction of the first end 112 of the bone plate 100. Further, such engagement between the first fixation element 128a and the wedge wall 120 can seek to pull the first fixation element 128a and the attached first bone segment 106a in an opposite direction, and more specifically in a direction toward the second bone segment 106b, the fracture site 104, and/or the second end 114 of the bone plate 100.

In at least some embodiments, as the first fixation element 128a continues to be at least transversally driven toward a seated position in the variable angle locking hole 102a, as illustrated in FIGS. 3 and 4C, the axial force generated by engagement between the head portion 136 of the first fixation element 128a and the wedge wall 120 can continue to axially displace at least the bone plate 100 and/or the first bone segment 106a in opposite directions until the central longitudinal axis 148 of the fixation element 128 is generally aligned with the central axis 118 of the variable angle locking hole 102a. Thus, in the present embodiment, as the bone plate 100 and/or the first bone segment 106a is/are axially displaced by engagement between the head portion 136 of the first fixation element 128a and the wedge wall 120, the first axial offset recess 126a can be displaced relative to at least a portion of the first fixation element 128a, such as the shank portion 134 and/or the head portion 136 of the first fixation element 128a, such that the central longitudinal axis 148a of the first fixation element 128a is generally aligned with the central axis 118a of the variable angle locking hole 10a.

As illustrated in at least FIG. 4C, according to certain embodiments, the variable angle locking hole 102a and/or the first fixation element 128a can be structured such that, at least when the first fixation element 128a approaches and/or reaches the seated position, the head portion 136 of the first fixation element 128a is generally recessed below or positioned relatively flush with the top side 108 of the bone plate 100. For example, according to certain embodiments, the wedge wall 120 can extend to a depth within the bone plate 100 beneath the top side 108 of the bone plate 100 that is sized to accommodate placement of the head portion 136 of the first fixation element 128a such that the first fixation element 128a minimally extends, if at all, beyond the top side 108 of the bone plate 100 when the first fixation element 128a is at the seated position.

FIG. 3 depicts an example of a second fixation element 128b being driven into the second bone segment 106b following the at least partial implantation of the first fixation element 128a in the first bone segment 106a. While, in the present example, the first fixation element 128a was at least initially positioned in at least a portion of the first axial offset recess 126a, the second fixation element 128b is shown as being at least initially positioned within at least a portion of the second axial offset recess 126b of another variable angle locking hole 102b. Accordingly, during at least initial implantation, the central longitudinal axis 148b of second fixation element 128b in the present example is offset to a side of the central axis 118b of the variable angle locking hole 102b that is generally opposite the side to which the central longitudinal axis 148a of the first fixation element 128a had been offset relative to the central axis 118a of the corresponding variable angle locking hole 102a, as illustrated in at least FIGS. 2, 4A and 4B. Thus, as the second fixation element 128b is driven into the second bone segment 106b, engagement between the head portion 136 of the second fixation element 128b and the adjacent portion of the wedge wall 120 can generate a force(s) that seeks to displace the bone plate 100 and/or the second bone segment 106b in opposite directions that are generally opposite to the directions at which the engagement of the first fixation element 128a and the wedge wall 120 sought to displace the bone plate 100 and/or the first bone segment 106a. For example, engagement between the head portion 136 of the second fixation element 128b and the wedge wall 120 can generate a force(s) that seeks to displace the bone plate 100 generally in the direction of the second end 114 of the bone plate 100. Further, such forces generated by engagement between the head portion 136 of the second fixation element 128b and the wedge wall 120 can seek to displace the second bone segment 106b generally in a direction toward the first end 112 of the bone plate 100, toward the fracture site 104, and/or toward the first bone segment 106a.

In addition to forces that can generate displacement of the bone plate 100, bone segments 106a, 106b, and/or bone 106, the forces generated by the engagement between the wedge wall 120 and the fixation elements(s) 128a, 128b can be used to retain the relative axial position(s) of bone segments 106a, 106b and/or the bone 106 and/or facilitate an axially compressive force being exerted at least onto the bone 106 and/or bone segments 106a, 106b. For example, in the examples illustrated in FIGS. 2-4C, besides providing forces that can displace the bone segments 106a, 106b and/or bone plate 100, the forces generated by engagement between the wedge wall 120 and the fixation elements(s) 128a, 128b can assist in providing compression or tension to the fracture site 104. Further, while the preceding examples were discussed with respect to bringing bone segments 106a, 106b together and/or providing compression or tension forces to the fracture site 104, for other situations, the first and second fixation elements 128a, 128b can be at least initially positioned on opposite sides of their respective variable angle locking holes 102a, 102b so as to at least assist in generating distraction, rather than compressive or tension forces. For example, the first fixation element 128a can be at least initially positioned in the second axial offset recess 126b of the associated variable angle locking hole 102a, and the second fixation element 128b can be at least initially positioned in the first axial offset recess 126a of the associated variable angle locking hole 102b so that the central longitudinal axes 148a, 148b of the first and second fixation devices 128a, 128b are each at least initially positioned between the fracture site 104 and the associated central axis 118 of their respective variable angle locking hole 102a, 102b. According to such an embodiment, engagement of the head portion 136 of each of the first and second fixation elements 128a, 128b with the adjacent portion of the wedge wall 120 can provide forces that at least assist in attempting to axially inwardly displace the bone plate 100 toward the fracture site 104, and thereby displace the first and second bone segments 106a, 106b in opposite directions and away from one another.

Figure 5:
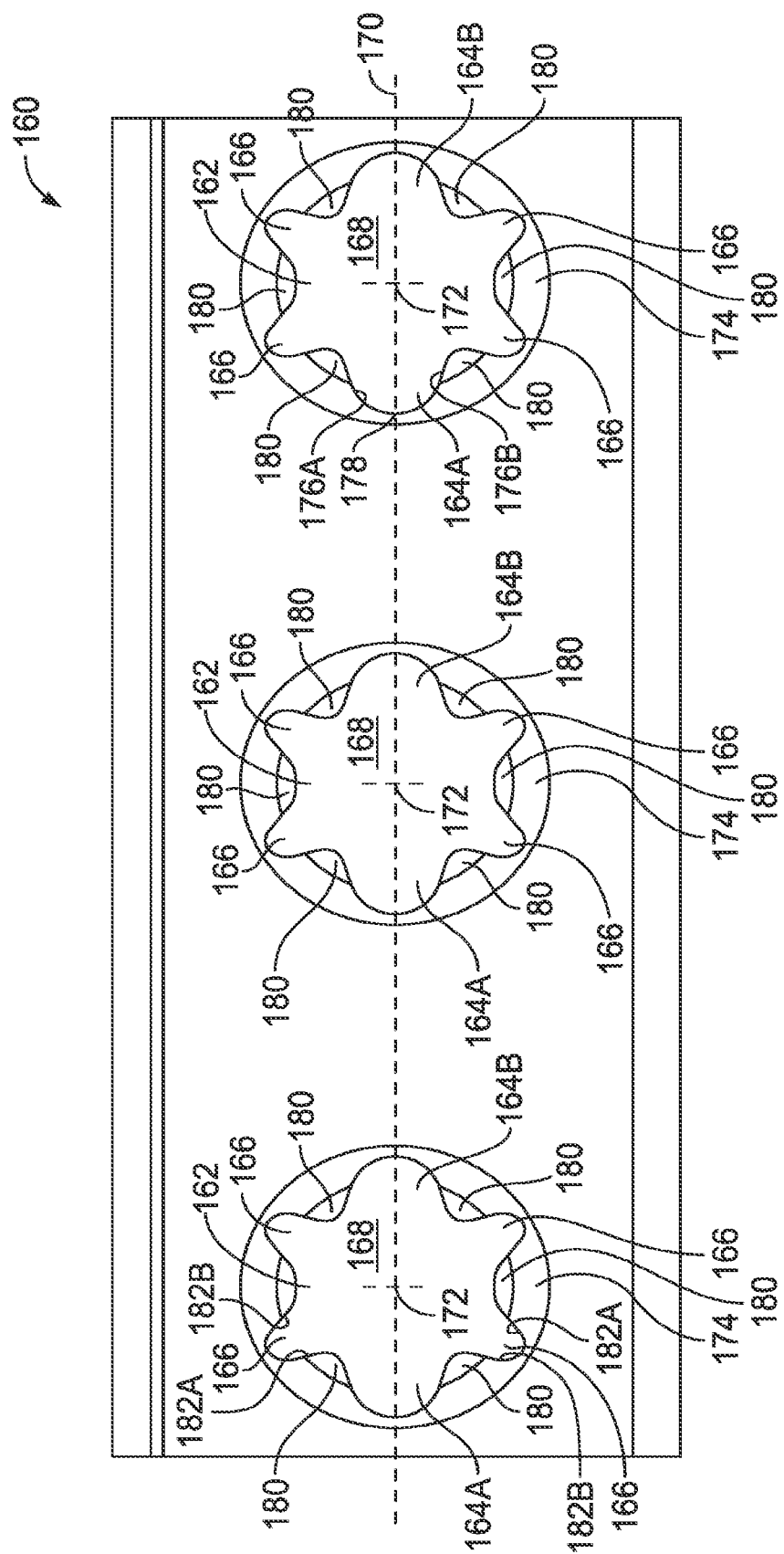
FIG. 5 illustrates a top view of a bone plate having variable angle locking holes structured to at least assist in facilitating axial compression and/or distraction of a bone fracture.
Figure 6A:
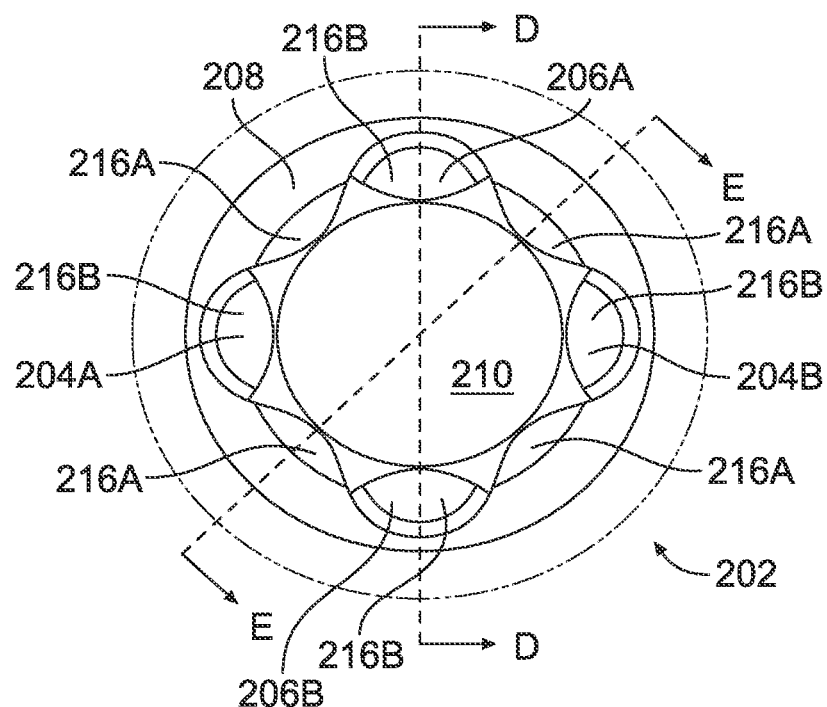
FIG. 6A illustrates a top view of an exemplary embodiment of a variable angle locking hole for a bone plate that is structured to at least assist in facilitating axial compression and/or distraction of a bone fracture site.
Figure 6B:
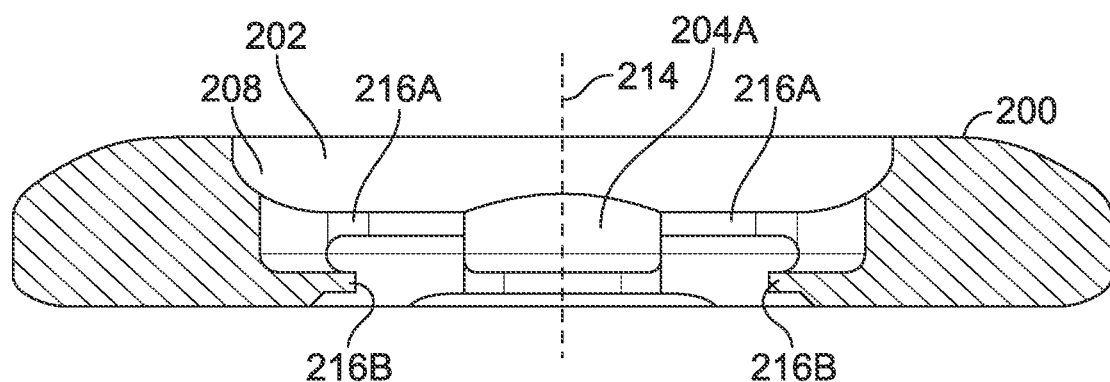
FIG. 6B illustrates a cross sectional view of the variable angle locking hole shown in FIG. 6A taken along line D-D and positioned within a bone plate.
Figure 6C:
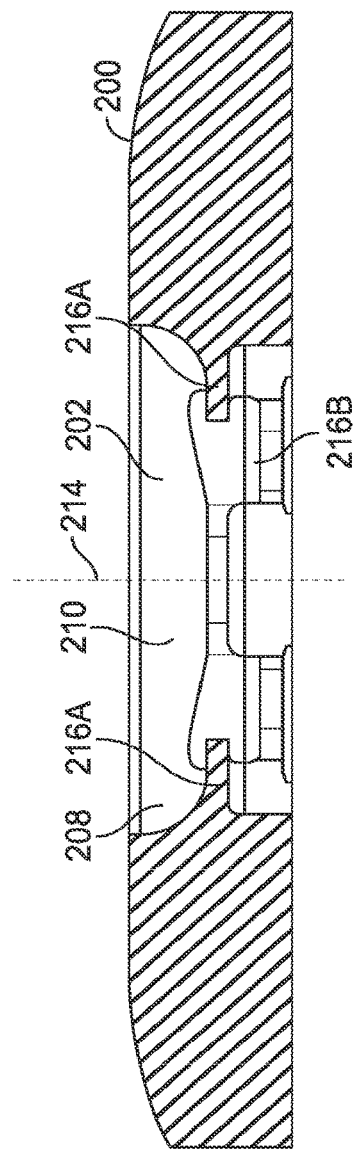
FIG. 6C illustrates a cross sectional view of the variable angle locking hole shown in FIG. 6A taken along line E-E and positioned within a bone plate.
Figure 6D:
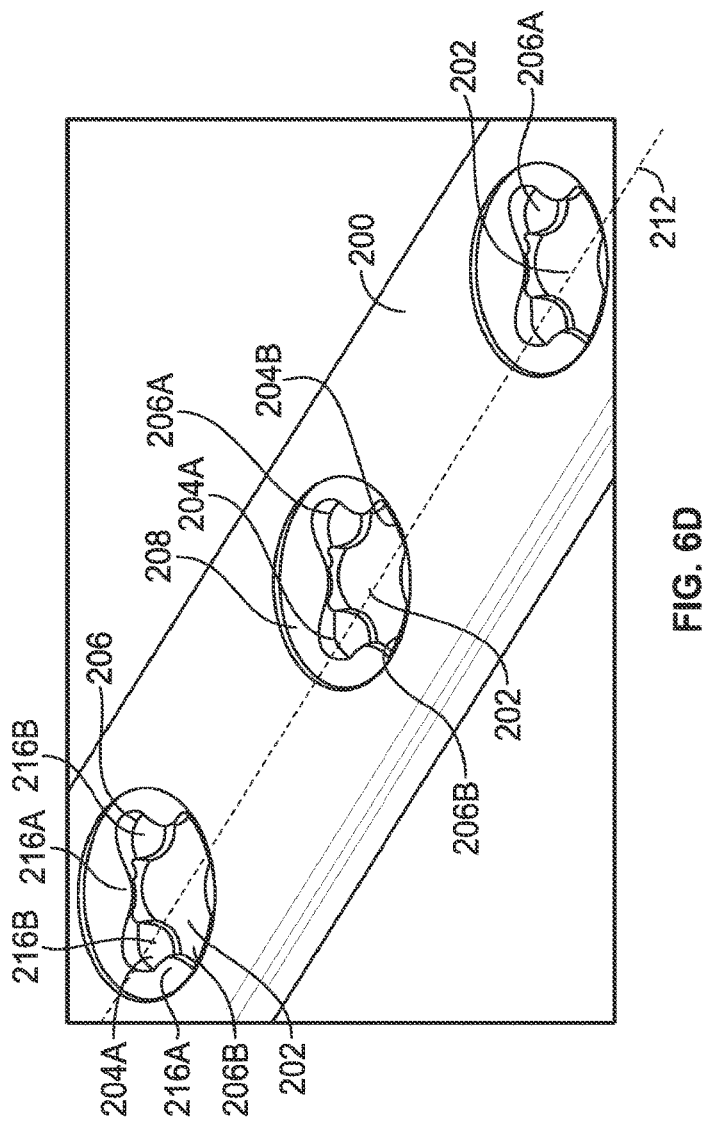
FIG. 6D illustrates a top side perspective view of the variable angle locking hole shown in FIG. 6A positioned within a bone plate.
Figure 7A:
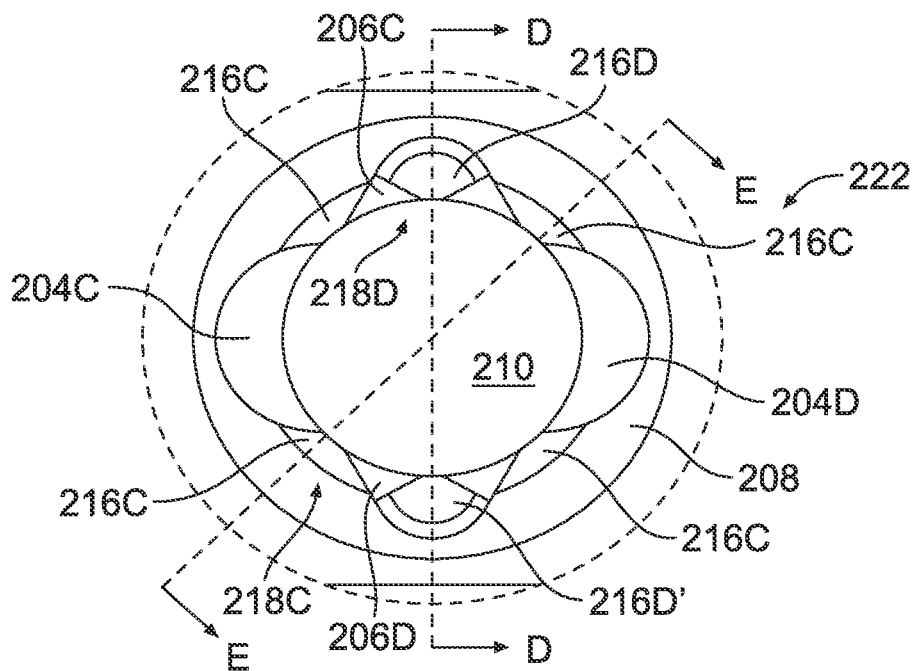
FIGS. 7A and 7B illustrate top and bottom side views, respectively, of an exemplary embodiment of a variable angle locking hole for a bone plate that is structured to at least assist in facilitating axial compression and/or distraction of a bone fracture site.
Figure 7B:
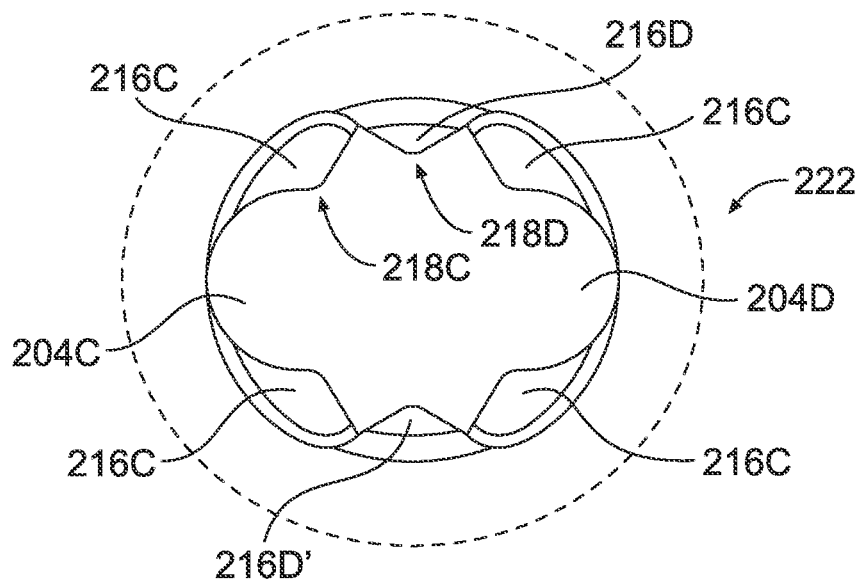
Figure 7C:
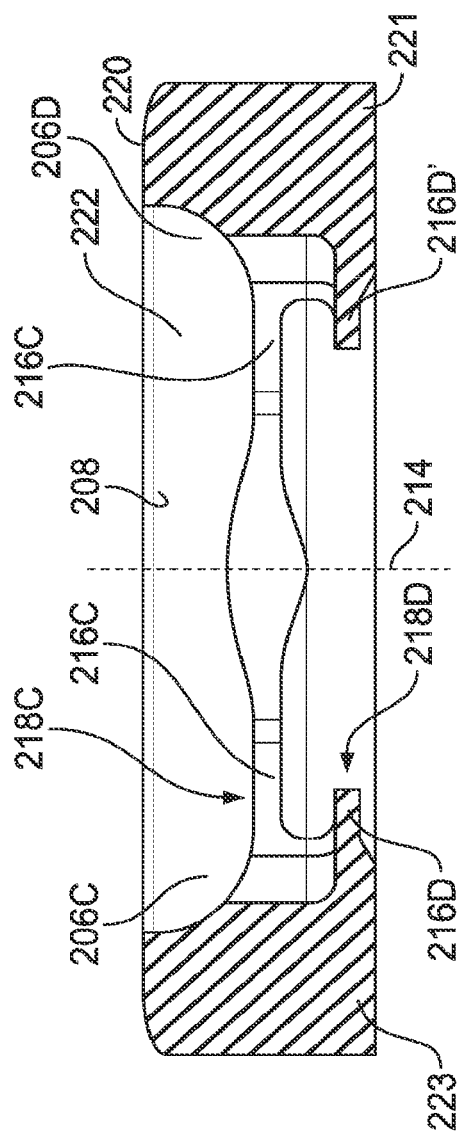
FIG. 7C illustrates a cross sectional view of the variable angle locking hole shown in FIG. 7A taken along line D-D and positioned within a bone plate.
Figure 7D:
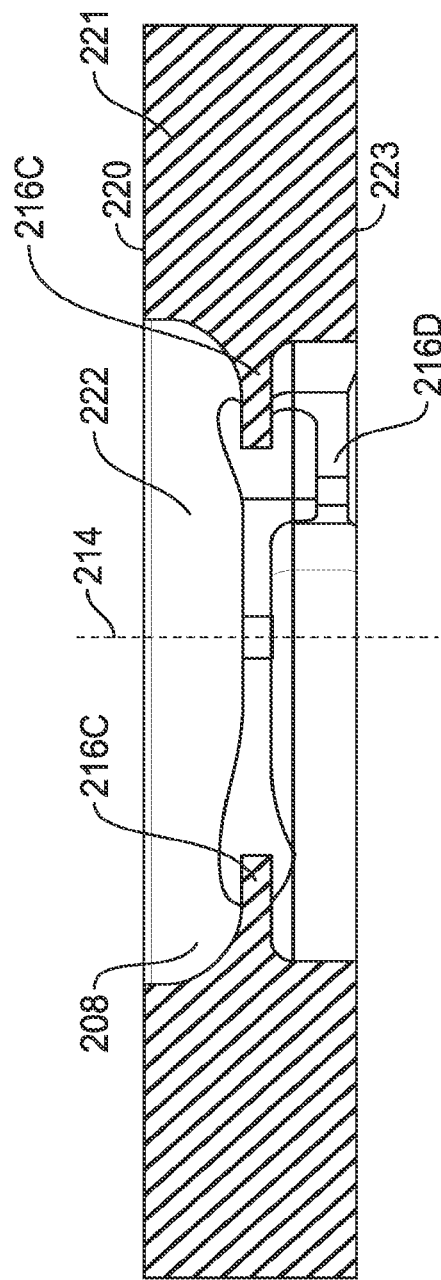
FIG. 7D illustrates a cross sectional view of the variable angle locking hole shown in FIG. 7A taken along line E-E and positioned within a bone plate.
Figure 7E:
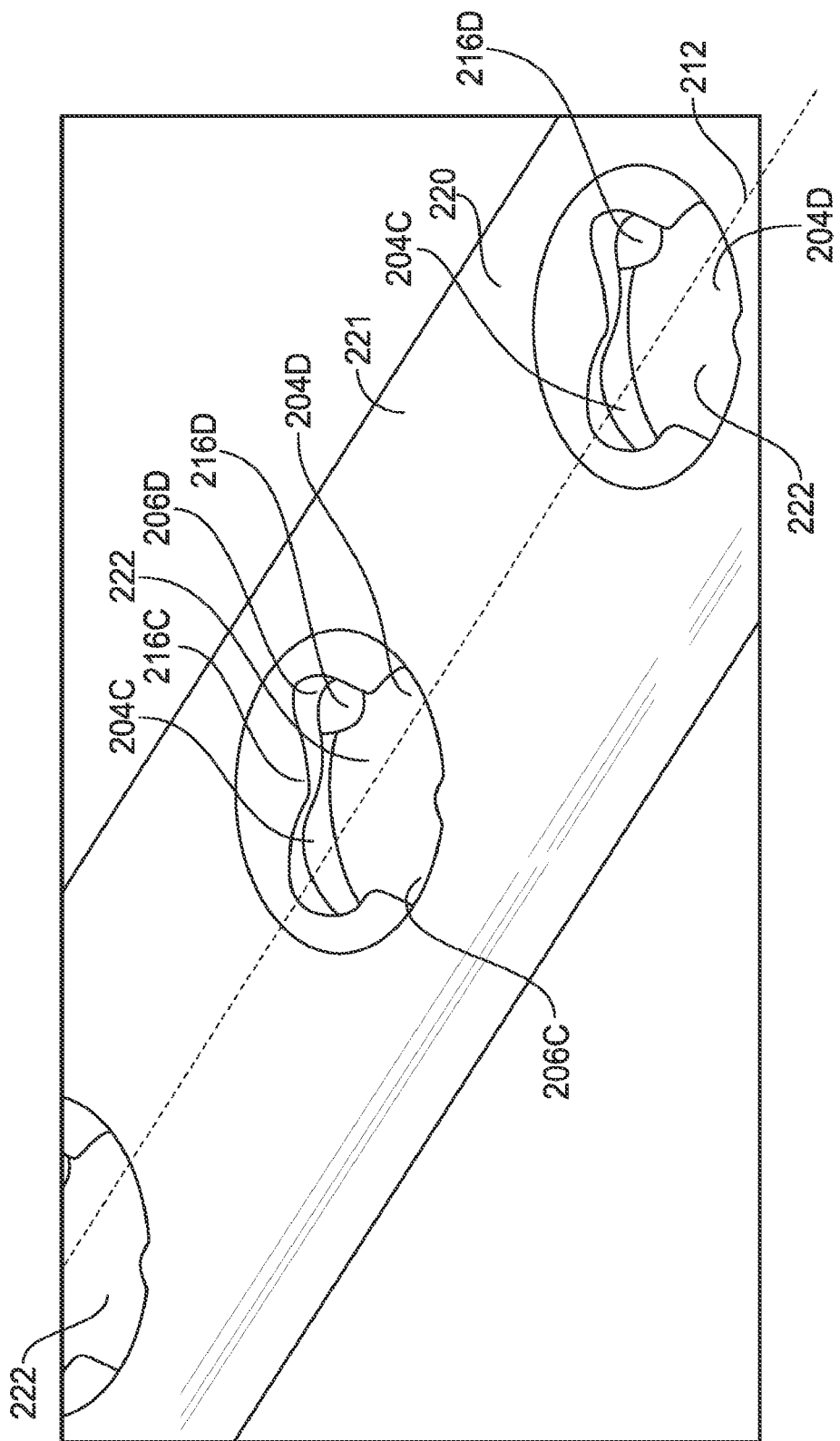
FIG. 7E illustrates a top side perspective view of the variable angle locking hole shown in FIG. 7A positioned within a bone plate.

FIG. 5 illustrates another exemplary embodiment of a bone plate 160 having variable angle locking holes 162. According to the depicted exemplary embodiment, the variable angle locking holes 162 include a first axial offset recess 164a, a second axial offset recess 164b, four angular positioning recesses 164, and a ramp or wedge wall 174. The first and second axial offset recesses 164a, 164b are positioned on opposite sides of the orifice 168 and generally extend in opposite directions along a central longitudinal axis 170 of the bone plate 160. Further, the first and second axial offset recesses 164a, 164b are sized to accommodate placement of at least a portion of a fixation element 128 therein and at locations that are offset from a central axis 172 of the variable angle locking hole 162. Thus, similar to the embodiments and examples discussed above with respect to FIGS. 1-4C, engagement between a fixation element 128 that is at an offset position relative to the central axis 172 of the variable angle locking hole 162 and the adjacent portion of the wedge wall 174 can at least assist in providing a force that axially displaces the bone plate 160 and/or the bone 106 or one or more bone segments 106a, 106b.

Compared to the embodiments discussed above with respect to FIGS. 1-4C, the distance between the first and second wall segments 176a, 176b of the first and second axial offset recesses 164a, 164b in the embodiment illustrated in FIG. 5 have been reduced, and the first and second wall segments 176a, 176b are arranged non-parallel to one another such that the first and second wall segments 176a, 176b each converge in a direction toward the end wall segment 178. Such a configuration can increase the size of the tabs 180 that are positioned between the first and second wall segments 176a, 176b and the angular positioning recesses 166, which can in turn increase the strength of the tabs 180. Moreover, by increasing the strength of the tabs 180, the strength of the locking engagement between the tabs 180 and the fixation element 128 can also be enhanced. Further, while the size of the first and second axial offset recesses 164a, 164b can be decreased when compared to the first and second axial offset recesses 126a, 126b illustrated in at least FIG. 1, the first and second axial offset recesses 164a, 164b illustrated in FIG. 5 can remain larger than the angular positioning recesses 166. For example, the distance between the first and second wall segments 176a, 176b of the first and second axial offset recesses 164a, 164b can be larger than a similar distance between opposing sidewalls 182a, 182b of the angular positioning recesses 166.

FIGS. 6A-6D illustrate another exemplary embodiment of a bone plate 200 having variable angle locking holes 202. As shown, the variable angle locking holes 202 include a first axial offset recess 204a and second axial offset recess 204b, a first and a second angular positioning recess 206a, 206b, and a ramp or wedge wall 208. Again, the first and second axial offset recesses 204a, 204b are positioned on opposing sides of the orifice 210 and generally extend in opposite directions along a central longitudinal axis 212 of the bone plate 200. Further, at least the first and second axial offset recesses 204a, 204b are sized to accommodate placement of at least a portion of a fixation element 128 therein and at locations that are offset from a central axis 214 of the variable angle locking hole 202. Thus, similar to the embodiments discussed above with respect to FIGS. 1-5, engagement between a fixation element 128 that is at an offset position relative to the central axis 214 of the variable angle locking hole 202 and the adjacent portion of the wedge wall 208 can at least assist in providing a force that axially displaces the bone plate 200, the bone 106, and/or or one or more bone segments 106a, 106b.

According to certain embodiments, the first and second angular positioning recesses 206a, 206b can be positioned on opposite sides of the central longitudinal axis 212 of the bone plate 200. Further, according to certain embodiments, the first and second angular positioning recesses 206a, 206b can have a size similar to that of the first axial offset recess 204a and second axial offset recess 204b. According to such an embodiment, the first and second angular positioning recesses 206a, 206b can be sized and positioned such that at least a portion of a fixation element can be positioned in the first and/or second angular positioning recesses 206a, 206b such that the central longitudinal axis 148 of the fixation element 128 is offset from the central axis 214 of the variable angle locking hole 202. In such situations, engagement between the fixation element 128 and the wedge wall 208 can at least linearly adjust the position of the bone plate 200 and/or associated bone 106 or bone segment 106a, 106b in a direction along the outer surface of the bone 106 that is generally perpendicular to the central axis 214 of the variable angle locking hole 202 and which is also non-parallel to the central longitudinal axis 212 of the bone plate 200. For example, in the illustrated embodiment, as the first and second angular positioning recesses 206a, 206b generally extend in directions that are perpendicular to the central longitudinal axis 212 of the bone plate 200, engagement of a fixation element 128 against a portion of the wedge wall 208 that is adjacent to either of the first or second angular positioning recesses 206a, 206b can displace the bone plate 200, bone 106, or bone segment 106a, 106b in a direction that is generally perpendicular to the central longitudinal axis 212 of the bone plate 200.

The bone plate 200 illustrated in FIGS. 6A-6D further includes a plurality of layers of tabs 216a, 216b. More specifically, the illustrated bone plate 200 includes a first layer 218a of one or more tabs 216a and a second layer 218b of one or more tabs 216b. As shown, the first layer 218a of tabs 216a can be positioned closer than the second layer 218b of tabs 216b relative to the top side 220 of the bone plate 200, and the second layer 218b of tabs 216b can be positioned closer than the first layer 218a of tabs 216a relative to the bottom side 223 of the bone plate 200. Additionally, according to certain embodiments, the first and second layers 218a, 218b of tabs 216a, 216b can be angularly offset from one another about the variable angle locking hole 202. For example, in the illustrated embodiment, the first layer 218a of tabs 216a can comprise tabs 216a that are positioned in a manner that separates the first and second axial offset recesses 204a, 204b from the adjacent first and second angular positioning recesses 206a, 206b. However, the second layer 218b of tabs 216b can comprise tabs 216b that each extend into a least a portion of the space or area of the first and second axial offset recesses 204a, 204b and/or the space or area of the first and second angular positioning recesses 206a, 206b, and can thus be located at positions that are angularly offset from the locations of the tabs 216a of the first layer 218a. Inclusion of additional tabs 216a, 216b such as, for example, via the second layer 218b of tabs 216b, can further enhance the strength of the locking engagement between the fixation element 128 and the tabs 216a, 216b.

While the embodiments illustrated in FIGS. 6A-6D include four tabs 216a, 216b in each of the first and second layers 218a, 218b, it should be understood that the number of tabs 216a, 216b for each layer 218a, 218b can vary. Further, the number of tabs 216a in the first layer 218a can be different than the number of tabs 216b in the second layer 218b. For example, FIGS. 7A-7E illustrate a bone plate 221 that includes variable angle locking holes 222 having a first layer 218c of tabs 216c that includes four tabs 216c that generally separate the first and second axial offset recesses 204c, 204d from the first and second angular positioning recesses 206c, 206d, and a second, lower layer 218d that includes two tabs 216d, 216d'. Further, although one of each of the two tabs 216d, 216d' of the second layer 218d is illustrated as being positioned in a space of the first and second angular positioning recesses 206c, 206d, respectively, according to other embodiments, at least one of the tabs 216d, 216d' can be positioned in space of at least one of the first and/or second axial offset recesses 204c, 204d.

FIGS. 8A-8F illustrate another embodiment of a bone plate 250 having variable angle locking holes 252 that include a ramp or wedge wall 254, opposite first and second axial offset recesses 256a, 256b, opposite first and second angular positioning recesses 258a, 258b, a first layer 260a of tabs 262a, and second layer 260b of tabs 262b. Further, the first layer 260a has a number of tabs 262a that is different from the number of tabs 262b of the second layer 260b. More specifically, in the embodiment illustrated in FIGS. 8A-8F, the first layer 260a has four tabs 262a, while the second layer 260bb has two tabs 26b.

Figure 8A:
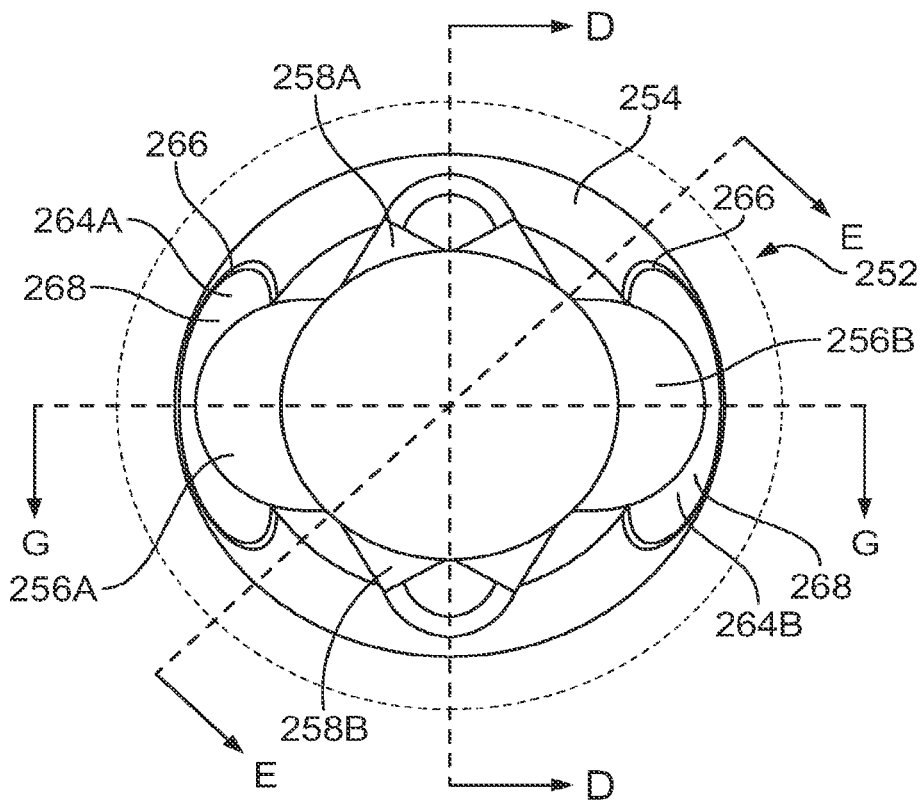
FIGS. 8A and 8B illustrate top and bottom side views, respectively, of an exemplary embodiment of a variable angle locking hole for a bone plate that is structured to at least assist in facilitating axial compression and/or distraction of a bone fracture site.
Figure 8B:
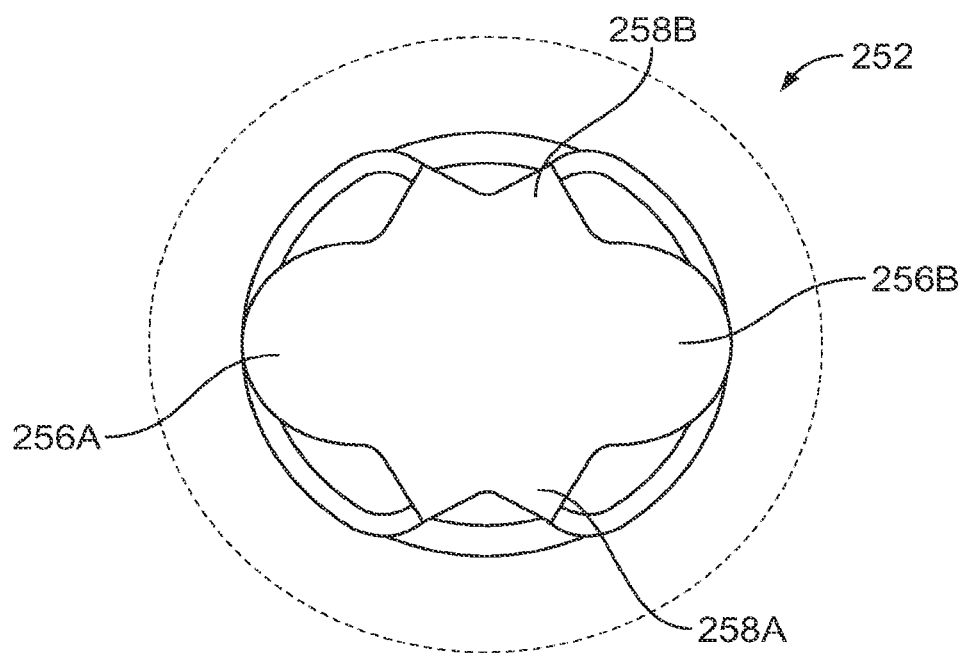
Figure 8C:
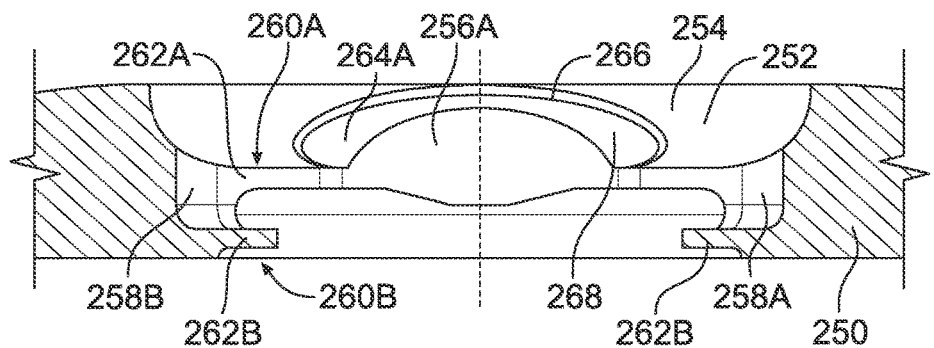
FIG. 8C illustrates a cross sectional view of the variable angle locking hole shown in FIG. 8A taken along line D-D and positioned within a bone plate.
Figure 8D:
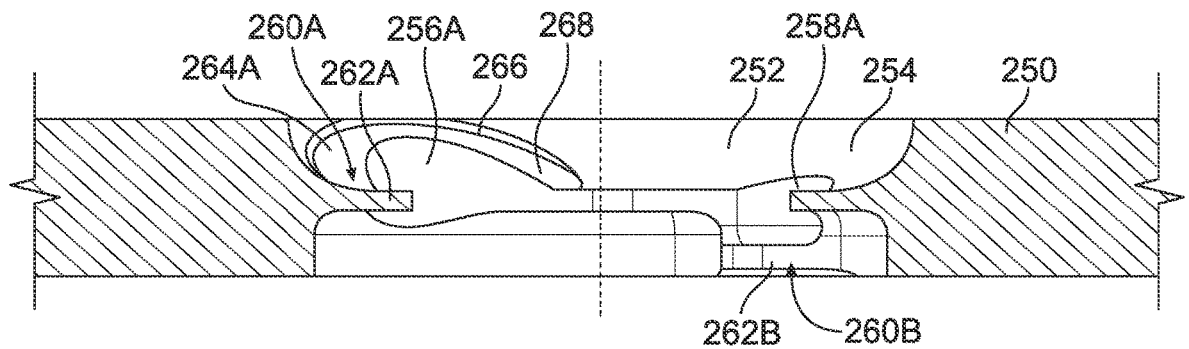
FIG. 8D illustrates a cross sectional view of the variable angle locking hole shown in FIG. 8A taken along line E-E and positioned within a bone plate.
Figure 8E:
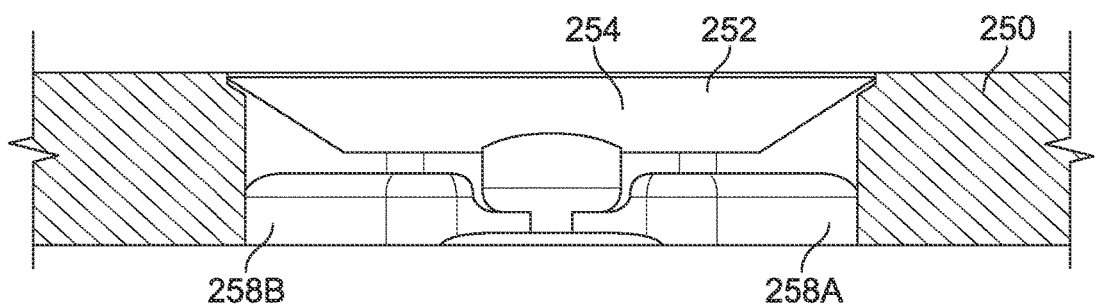
FIG. 8E illustrates a cross sectional view of the variable angle locking hole shown in FIG. 8A taken along line G-G and positioned within a bone plate.
Figure 8F:
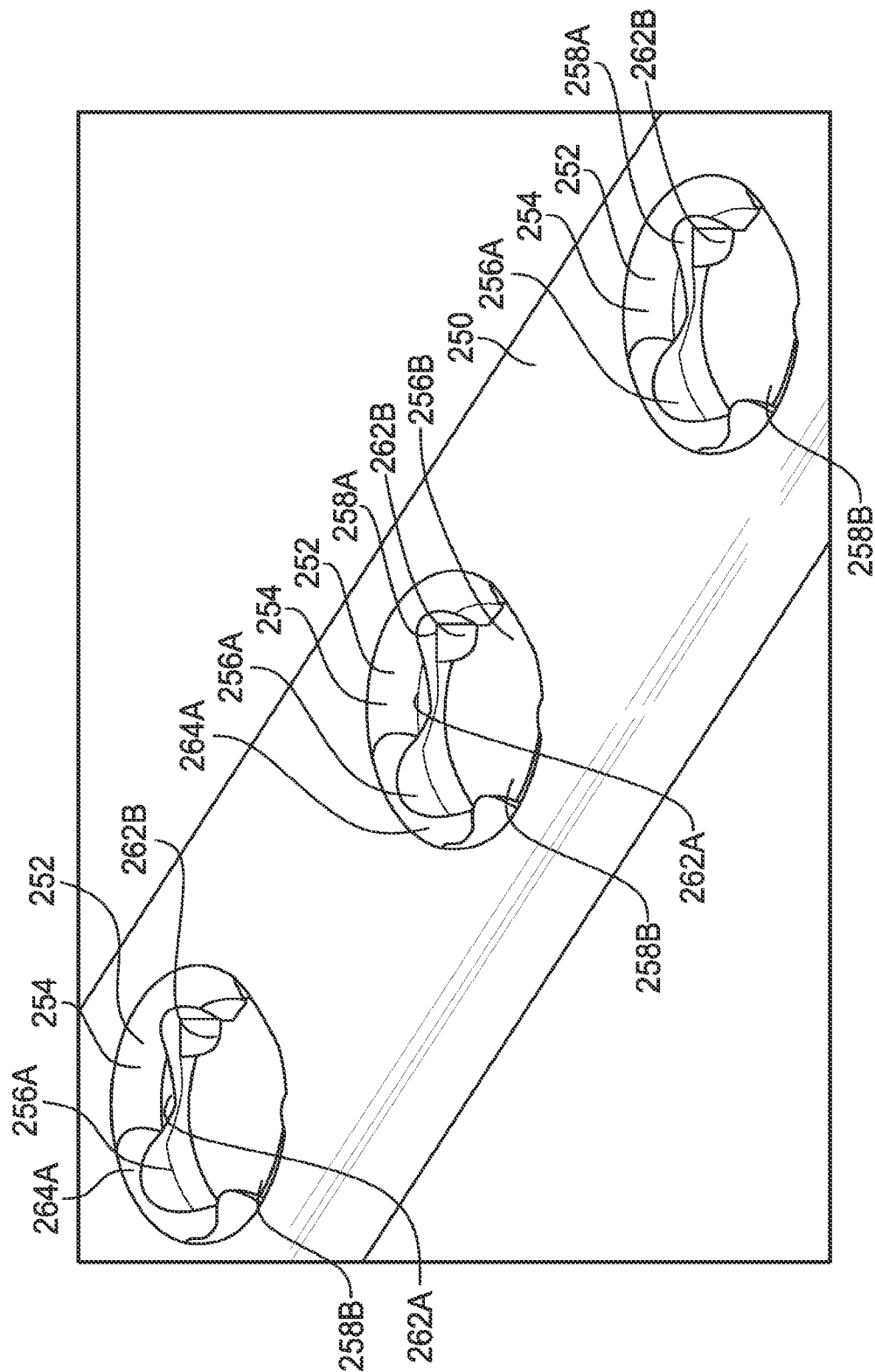
FIG. 8F illustrates a top side perspective view of the variable angle locking hole shown in FIG. 8A positioned within a bone plate.

Further, as illustrated in at least FIGS. 8A, 8C and 8D, the wedge wall 254 includes first and second compression ramps 264a, 264b that are positioned in a portion of the wedge wall 254 that extends around the first axial offset recess 256a and the second axial offset recess 256b, respectively. According to certain embodiments, the compression ramps 264a, 264b can be configured as a recess or groove in the wedge wall 254 that extends about at least a portion of the associated first and second axial offset recess 256a, 256b. Further, according to certain embodiments, the compression ramps 264a, 264b can have a shape or size that is generally similar to at least a portion of the fixation element 128. For example, according to certain embodiments, the compression ramps 264a, 264b can have a size that accommodates the placement of a portion of the head portion 136 of the fixation element 128. Further, the compression ramps 264a, 264b can be configured to further facilitate the linear compressive force exerted by the fixation element 128 against the bone plate 250, and thereby further facilitate axial displacement of the bone plate 250 relative to at least the fixation element 128 and/or axial displacement of the corresponding bone 106 relative to the bone plate 250 and/or the formation of axially compressive or distraction forces.

The compression ramps 264a, 264b can include a wall portion 266 and a ramp portion 268, with the wall portion 266 extending about at least a portion of the ramp portion 268 and positioned between the adjacent portion of the wedge wall 254 and the ramp portion 268. According to certain embodiments, the wall portion 266 can extend in a generally vertical direction. However, according to other embodiments, the wall portion 266 can be angled or sloped so as to provide a transition between the wedge wall 254 and the lower or recessed ramp portion 268 of the compression ramps 264a, 264b. Further, according to certain embodiments, the ramp portion 268 can extend along an incline or slope that is, or alternatively is not, similar to the incline or slope of the adjacent portion of the wedge wall 254.

Figure 9A:
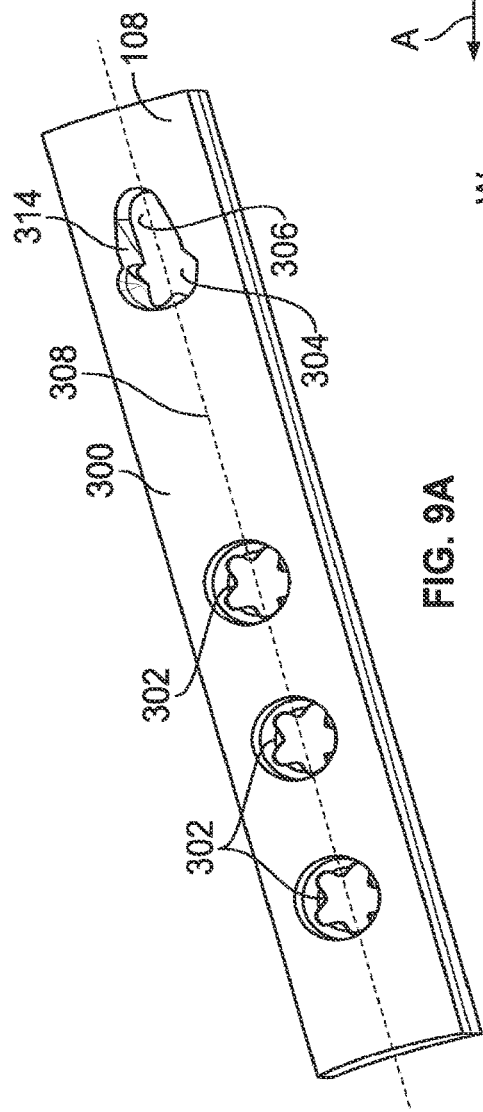
FIG. 9A illustrates a top side perspective view of a bone plate having both static variable angle locking holes and a variable angle locking hole having a compression slot.
Figure 9C:
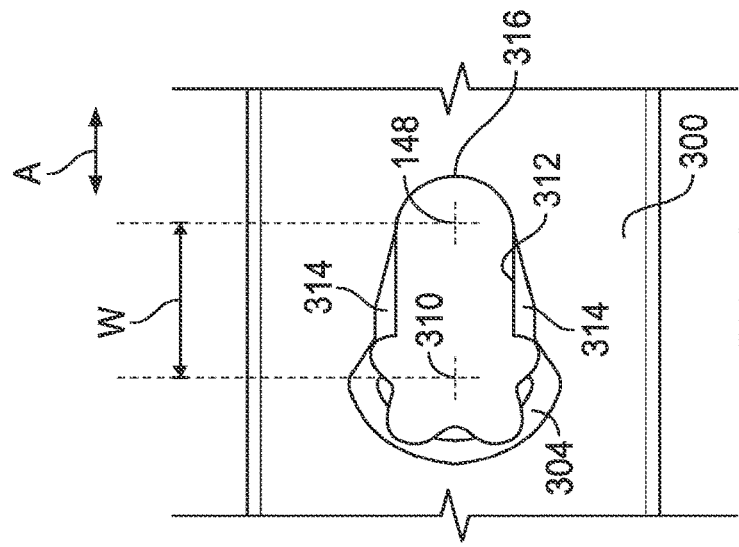
FIGS. 9B and 9C illustrate top side perspective and top side views, respectively, of the variable angle locking hole having a compression slot, as shown in FIG. 9A, that includes a pair of compression ramps.
Figure 9B:
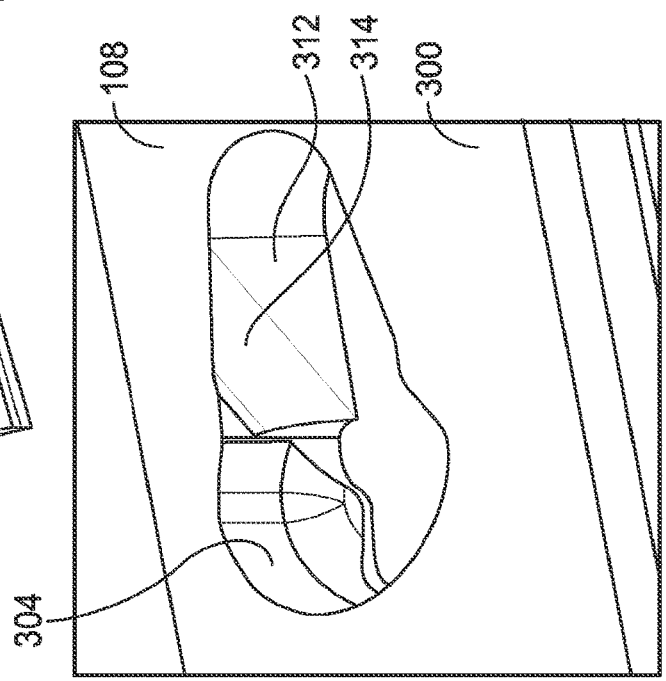

FIGS. 9A-9C illustrate a bone plate 300 having one or more static variable angle locking holes 302 and at least one variable angle locking hole 304 that includes at least one compression slot 306 that extends along the central longitudinal axis 308 of the bone plate 300. The compression slot 306 can be generally defined by an inner wall 312 that extends through at least a portion of the bone plate 300. Further, opposing sides of the inner wall 312 of the compression slot 306 can each include a compression ramp 314.

The compression ramps 314 can be inwardly sloped or inclined in a general direction away from the top side 108 of the bone plate 300 as the compression ramps 314 extends away from an end portion 316 of the compression slot 306.

As illustrated in FIG. 9C, a fixation element 128 (FIG. 4A) driven into a bone 106 can at least initially be positioned in the compression slot 306 such that the central longitudinal axis 148 of the fixation element 128 is offset from the central axis 310 of the variable angle locking hole 304. Similar to previously discussed embodiments, as the fixation element 128 proceeds to be driven into the bone 106, a portion of the fixation element 128, such as the head portion 136 of the fixation element 128, can be at least transversally displaced toward the bone plate 300 and come into contact with the compression ramps 314. Such contact of the fixation element 128 with the inclined or sloped surface of the compression ramps 314 can facilitate axial displacement such as, for example, sliding of the bone plate 300 in an axial direction (as indicated by the "A" direction in FIG. 9C) toward the central longitudinal axis 148 of the fixation element 128 and/or facilitate axial displacement the bone 106 generally in a direction toward the central axis 310 of the variable angle locking hole 304. More specifically, such engagement between the fixation element 128 and the bone plate 300 can facilitate axial displacement of the bone plate 300 and/or bone 106 such that the central longitudinal axis 148 of the fixation element 128 and the central axis 310 of the variable angle locking hole 304 are generally aligned or in closer proximity to one another. Further, the extent to which the relative axial displacement that can be attained to bring the central longitudinal axis 148 of the fixation element 128 and the central axis 310 of the variable angle locking hole 304 into alignment or in closer proximity to one another can be influenced by the operable length of the compression slot 306, and by the possible initial distance (as indicated by "W" in FIG. 9C) between central longitudinal axis 148 of the fixation element 128 and the central axis 310 of the variable angle locking hole 304.

Figure 10A:
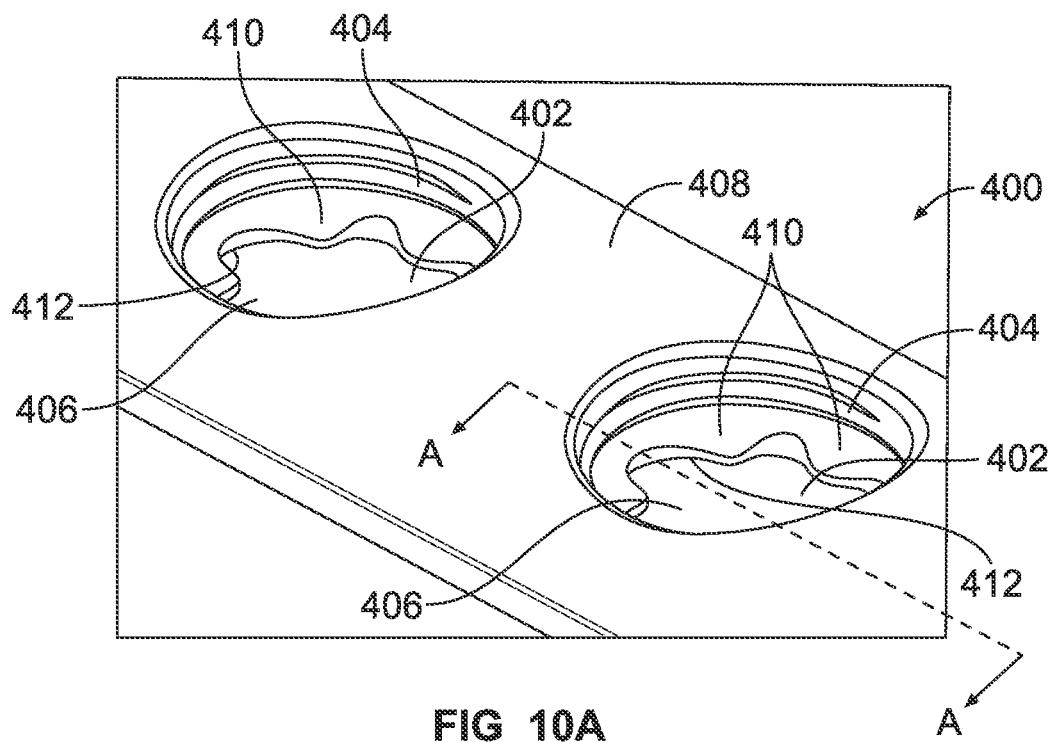
FIG. 10A illustrates a top side perspective view of an exemplary embodiment of a combination fixed-variable angle locking hole that is adapted for engagement with a locking fixation element in connection with a bone plate that accommodates axial compression and/or distraction of a bone fracture site.
Figure 10B:
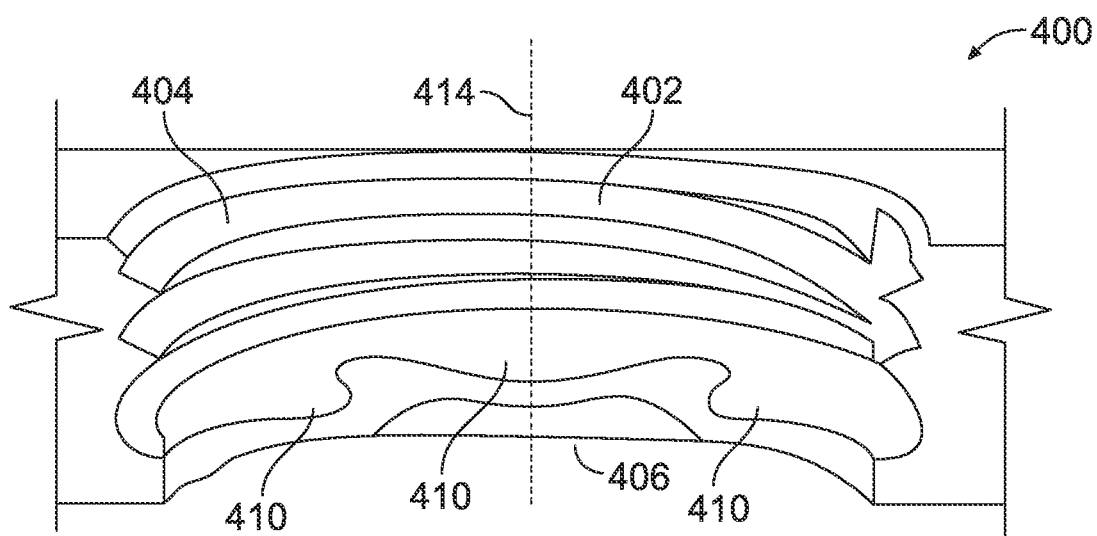
FIG. 10B is a cross sectional view of a combination fixed-variable angle locking hole taken along line A-A of FIG. 10A.

FIGS. 10A and 10B illustrate another embodiment of a bone plate 400 having a combination fixed-variable angle hole 402 that is adapted to engage a locking or non-locking fixation element and assist in the formation of axial compression or tension along the bone plate 400 and/or bone 106. The bone plate 400 can be structured such that, in certain situations, at least one of the variable angle holes 402 illustrated in FIGS. 10A and 10B can be positioned on one side of a fracture site 104 to receive a locking screw such as, for example, a locking screw that has a thread on an outer surface of the head portion 136 of the locking screw, while, on an opposite side of the fracture site 104, at least one other combination fixed-variable angle hole 402 receives either a locking or non-locking screw and/or the previously discussed variable angle holes 102, 162, 202, 222, 252, 304 receives a non-locking fixation element.

According to certain embodiments, the combination fixed-variable angle hole 402 of FIGS. 10A and 10B is structured to at least assist in the locking screw exerting a compressive force against the bone 106, while, for example, also retaining the position of the locking screw in the fixed-variable angle hole 402 as the engagement between the non-locking screw and the associated variable angle hole 102, 162, 202, 222, 252, 304 facilitates the formation of axial compressive or tensile forces about the bone plate 400 and/or the bone 106, as previously discussed. For example, according to certain embodiments, the fixed-variable angle hole 402 can be structured such that the locking screw engages the combination fixed-variable angle hole 402 in a manner that prevents the locking screw from being pulled out of the bone 106 as a non-locking screw on an opposite side of the fracture site 104 that is being driven into the bone 106 operably engages with a wedge wall 120, 174, 208, 254 or compression ramps 264a, 264b of the variable angle hole 102, 162, 202, 222, 252, 304, as previously discussed. Moreover, the combination fixed-variable angle hole 402 can be sized so as to prevent or limit movement of the combination fixed-variable angle hole 402 relative to the locking screw as engagement of the non-locking screw with the wedge wall 120, 174, 208, 254 or compression ramps 264a, 264b on the opposite side of the fracture site 104 generates forces that can axially displace or deform the bone plate 400 and/or bone 106.

According to the illustrated embodiment, the combination fixed-variable angle hole 402 includes an inner wall 404 that generally defines an orifice 406 of the fixed-variable angle hole 402. The orifice 406 can be sized to accommodate passage of a portion of the fixation element such as, for example, a threaded or non-threaded shank portion 134, through the fixed-variable angle hole 402. Further, the orifice 406 can be sized such that the fixation element fixation generally does not extend beyond a top side 408 of the bone plate 400. For example, referencing FIGS. 3, 10A, and 10B, the orifice 406 can be sized such that the head portion 136 of the first fixation element 128a that can be positioned in the combination fixed-variable angle hole 402 is generally recessed below, or relatively flush with, the top side 408 of the bone plate 400.

As illustrated in FIGS. 10A and 10B, the fixed-variable angle hole 402 can include a plurality of tabs 410 that inwardly extend from the inner wall 404, and which are separated from adjacent tabs 410 by a recess 412. The tabs 410 can be sized such that a portion of the fixation element can, in at least certain embodiment, including but not limited to when the fixation element is a non-locking screw, securely engage one or more of the tabs 410. Further, the tabs 410 can be sized to provide interference that prevents at least a portion of the fixation element such as, for example, a head portion 136, from being pulled through the entire orifice 406. Further, the recesses 412 can accommodate at least the angular positioning of the fixation element into the variable angle holes 402 such as, for example, a locking or non-locking screw passing into the fixed-variable angle hole 402 at an angle that is non-parallel to a central axis 414 of the fixed-variable angle hole 402. Further, according to certain embodiments, two or more of the recesses 412, and thus two or more of the tabs 410, can have different sizes such as, for example, different widths, than other tabs 410 and recesses 412. For example, according to some embodiments, the recesses 412 that are positioned generally along a longitudinal axis 415 of the bone plate 400 can provide a larger space between adjacent tabs 410 than is provided by other recesses 412. Additionally, while the variable angle holes 402 can be structured to provide a variety of different number tabs 410 and associated recesses 412, according to the illustrated embodiment, the fixed-variable angle hole 402 has six recesses 412.

The combination fixed-variable angle hole 402 further includes a plurality of projections 416 that inwardly extend from the inner wall 404, and which are positioned between the tabs 410 and a top side 408 of the bone plate 400. According to certain embodiments, the plurality projections 416 can matingly engage the fixation element in a manner that can at least assist in lockingly securing the fixation element to the bone plate 106 and/or compressing the bone plate 400 against the bone 106. Additionally, according to certain embodiments, the plurality of projections 416 can provide a thread that mates with a threaded portion of a head portion 136 of the fixation element such as, for example, a threaded portion of the head portion 136 of a locking screw. For example, referring to FIGS. 3, 10A and 10B, in at least certain embodiments, the fixation element can be a locking screw and can be operably secured in the combination fixed-variable angle hole 402 such that the central longitudinal axis 148a of the fixation element is generally aligned and/or parallel with the central axis 414 of the fixed-variable angle hole 402. In such situations, threads on the outer surface of the head portion 138 of the locking screw can threadingly engage the thread provided by the plurality of projections 416 of the fixed-variable angle hole 402. Alternatively, as discussed above, the fixed-variable angle hole 402, including the recesses 412 and tabs 410, can be configured such that a fixation element, which can be a locking or non-locking screw, can be operably positioned in the fixed-variable angle hole 402 at a variety of different angles that are not parallel to the central axis 414 of the fixed-variable angle hole 402. In such situations, the threads of the locking screw can still engage or abut the projections 416 in a non-threaded manner without subsequent procedures to build-up of the head portion 136 of the locking screw. Additionally, in at least certain embodiments, such non-threaded engagement of the plurality of projections 416 with the locking screw, or alternatively a non-locking screw, can assist in retaining the position of the fixation element and/or the fixed-variable angle hole 402 while the bone plate 400 and/or bone 106 is subjected to axial compression or distraction by engagement of another fixation device with a wedge wall 120, 174, 208, 254 or compression ramps 264a, 264b of the variable angle hole 102, 162, 202, 222, 252, 304, as previously discussed.

While the invention has been described in connection with what is presently considered to be the most practical and preferred embodiment, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law.

It should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

The invention claimed is:

1. A bone plate configured to receive at least one fixation element to secure the bone plate to at least one bone segment, the bone plate comprising:
   a first end and a second end, the bone plate extending axially between the first and second ends along a central longitudinal axis of the bone plate; and
   an elongated variable angle hole including a length extending a first distance as measured along the central longitudinal axis and a width having a second distance as measured perpendicular to the central longitudinal axis, the first distance being greater than the second distance, the elongated variable angle hole further including:
   a plurality of inwardly extending tabs on each side of the central longitudinal axis extending and spaced circumferentially about the variable angle hole, and recesses, the plurality of inwardly extending tabs including first and second layers of tabs, the first layer of tabs being positioned in closer proximity to a top surface of the bone plate than the second layer of tabs, each tab in the first layer of tabs being circumferentially separated from adjacent tabs in the first layer of tabs by a respective one of the recesses, each tab in the second layer of tabs being circumferentially separated from adjacent tabs in the second layer of tabs by a respective one of the recesses, the plurality of inwardly extending tabs comprising non-threaded protruding tabs and the recesses comprising concave recesses, wherein the elongated variable angle hole comprises a series of the non-threaded protruding tabs separated by the concave recesses, the non-threaded protruding tabs being arranged and configured to engage a corresponding space between adjacent threads formed on a head portion of the at least one fixation element for securing a position of the at least one fixation element relative to the bone plate;
   wherein all of the tabs in the first layer of tabs are circumferentially offset relative to all of the tabs in the second layer of tabs; and
   wherein the first distance and the second distance are measured between opposed ones of the recesses such that the elongated variable angle hole defines an elongated slot extending along the central longitudinal axis.

2. The bone plate of claim 1, wherein the second layer of tabs includes two tabs.

3. The bone plate of claim 2, wherein the first layer of tabs includes a same number of tabs as the second layer of tabs.

4. The bone plate of claim 2, wherein the first layer of tabs includes a different number of tabs as the second layer of tabs.

5. The bone plate of claim 1, wherein the second layer of tabs consists of first and second tabs.

6. The bone plate of claim 5, wherein the first layer of tabs includes a different number of tabs as the second layer of tabs.

7. The bone plate of claim 6, wherein the first layer of tabs consists of first, second, third, and fourth tabs.

8. The bone plate of claim 1, wherein the first layer of tabs includes a greater number of tabs than the second layer of tabs.

9. The bone plate of claim 1, wherein the recesses include at least one axial offset recess sized and configured to receive insertion of at least a portion of the at least one fixation element at a location in the elongated variable angle hole at which a central axis of the received fixation element is axially offset by an offset distance from a central axis of the elongated variable angle hole.

10. The bone plate of claim 9, wherein the at least one axial offset recess includes a first axial offset recess and a second axial offset recess, the first and second axial offset recesses extending in opposite directions along the central longitudinal axis of the bone plate.

11. The bone plate of claim 9, wherein the elongated variable angle hole further includes a wedge wall having a shape and size configured to be engaged by at least a portion of the received fixation element to axially displace the bone plate and the received fixation element relative to each other in opposite directions that decreases the offset distance between the central axis of the received fixation element and the central axis of the elongated variable angle hole.

12. The bone plate of claim 11, wherein the wedge wall further includes a compression ramp positioned about the at least one axial offset recess.

13. A bone plate configured to receive at least one fixation element to secure the bone plate to at least one bone segment, the bone plate comprising:

a first end and a second end, the bone plate extending axially between the first and second ends along a central longitudinal axis of the bone plate; and an elongated variable angle hole including a length extending a first distance as measured along the central longitudinal axis and a width having a second distance as measured perpendicular to the central longitudinal axis, the first distance being greater than the second distance, the elongated variable angle hole further including:

a first layer of inwardly extending tabs;

a second layer of inwardly extending tabs, the first layer of inwardly extending tabs being positioned in closer proximity to a top surface of the bone plate than the second layer of inwardly extending tabs; and recesses;

wherein:

the second layer of inwardly extending tabs includes first and second tabs, the first tab being circumferentially separated from the second tab by one of the recesses;

the first layer of inwardly extending tabs includes a same number of tabs as the second layer of inwardly extending tabs, adjacent tabs of the first layer of inwardly extending tabs being circumferentially separated by a respective one of the recesses;

the tabs in the first and second layers of inwardly extending tabs comprising non-threaded protruding tabs and the recesses comprising concave recesses, wherein the elongated variable angle hole comprises a series of the non-threaded protruding tabs separated by the concave recesses, the non-threaded protruding tabs being arranged and configured to engage a corresponding space between adjacent threads formed on a head portion of the at least one fixation element for securing a position of the at least one fixation element relative to the bone plate; and all of the tabs in the first layer of inwardly extending tabs are circumferentially offset relative to all of the tabs in the second layer of inwardly extending tabs;

wherein the first distance and the second distance are measured between opposed ones of the recesses such that the elongated variable angle hole defines an elongated slot extending along the central longitudinal axis.

\* \* \* \* \*